US012558688B2

(12) United States Patent
Olsson et al.

(10) Patent No.: US 12,558,688 B2
(45) Date of Patent: *Feb. 24, 2026

(54) MICROFLUIDIC DEVICE AND METHOD

(71) Applicant: QUIDEL CARDIOVASCULAR INC., San Diego, CA (US)

(72) Inventors: Erik Mikael Olsson, Uppsala (SE); Austin Derfus, Solana Beach, CA (US); Armando Tovar, San Diego, CA (US); Justin Davidson, San Diego, CA (US); Tuan Do, San Diego, CA (US); Paul Crivelli, San Diego, CA (US); Matthew Wang, San Diego, CA (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 902 days.

This patent is subject to a terminal disclaimer.

(21) Appl. No.: 17/072,332

(22) Filed: Oct. 16, 2020

(65) Prior Publication Data

US 2021/0031196 A1 Feb. 4, 2021

Related U.S. Application Data

(63) Continuation of application No. 16/085,997, filed as application No. PCT/US2017/023094 on Mar. 17, 2017, now Pat. No. 10,835,898.

(Continued)

(51) Int. Cl.
*G01N 33/50* (2006.01)
*B01L 3/00* (2006.01)
(Continued)

(52) U.S. Cl.
CPC ... *B01L 3/502746* (2013.01); *B01L 3/502723* (2013.01); *G01N 33/491* (2013.01);
(Continued)

(58) Field of Classification Search
CPC ......... B01L 3/502746; B01L 3/502723; G01N 33/491; G01N 33/54306; G01N 33/6887
See application file for complete search history.

(56) References Cited

U.S. PATENT DOCUMENTS 6,302,134 B1 10/2001 Kellogg et al.
6,663,833 B1 * 12/2003 Stave ............... G01N 33/54388
436/178

(Continued)

FOREIGN PATENT DOCUMENTS

CN 101623660 A 1/2010
EP 1967266 A1 * 9/2008 .......... B01F 25/4337
(Continued)

OTHER PUBLICATIONS

Furuberg, Liv, et al. "RNA amplification chip with parallel microchannels and droplet positioning using capillary valves." Microsystem Technologies 14 (2008): 673-681. (Year: 2008).*

(Continued)

*Primary Examiner* — Bao-Thuy L Nguyen
*Assistant Examiner* — Jim Atwell
(74) *Attorney, Agent, or Firm* — McDermott Will & Schulte LLP; Brennen P. Baylor; Judy M. Mohr

(57) ABSTRACT

A combination of components in a capillary flow channel uses capillary forces to passively control the movement of liquid samples within a microfluidic device. To detect a target, a liquid sample introduced to a proximal portion of capillary channel of a microfluidic device moves by capillary action along the specific components of capillary channel.

23 Claims, 14 Drawing Sheets

Related U.S. Application Data

(60) Provisional application No. 62/310,640, filed on Mar. 18, 2016.

(51) Int. Cl.

| | | |
|---|---|---|
| *G01N 33/49* | (2006.01) | |
| *G01N 33/543* | (2006.01) | |
| *G01N 33/68* | (2006.01) | |

(52) U.S. Cl.

CPC ... *G01N 33/54306* (2013.01); *G01N 33/6887* (2013.01); *B01L 2200/16* (2013.01); *B01L 2300/0681* (2013.01); *B01L 2300/0816* (2013.01); *B01L 2300/0867* (2013.01); *B01L 2300/0883* (2013.01); *B01L 2400/0406* (2013.01); *B01L 2400/0487* (2013.01); *B01L 2400/0688* (2013.01); *B01L 2400/088* (2013.01)

(56) References Cited

U.S. PATENT DOCUMENTS

| | | | | |
|---|---|---|---|---|
| 7,347,617 | B2 | 3/2008 | Pugia et al. | |
| 7,479,393 | B2 | 1/2009 | Noetzel et al. | |
| 7,771,989 | B2 | 8/2010 | Wang | |
| 7,824,611 | B2 | 11/2010 | Buechler | |
| 9,168,524 | B2 | 10/2015 | Rothacher et al. | |
| 9,255,866 | B2 | 2/2016 | Dirckx et al. | |
| 2005/0041525 | A1* | 2/2005 | Pugia | B01L 3/502746 |
| | | | | 366/341 |
| 2010/0009430 | A1 | 1/2010 | Wan et al. | |
| 2010/0065427 | A1 | 3/2010 | Fujita | |
| 2010/0112723 | A1* | 5/2010 | Battrell | G01N 33/53 |
| | | | | 422/68.1 |
| 2010/0261286 | A1 | 10/2010 | Kim et al. | |
| 2011/0076692 | A1* | 3/2011 | Sista | G01N 33/6893 |
| | | | | 435/7.1 |
| 2012/0121480 | A1 | 5/2012 | Frenz et al. | |
| 2012/0171698 | A1 | 7/2012 | Yager et al. | |
| 2012/0273702 | A1 | 11/2012 | Culbertson et al. | |
| 2013/0023060 | A1 | 1/2013 | Klaunik et al. | |
| 2014/0220668 | A1 | 8/2014 | Tachibana et al. | |
| 2015/0017737 | A1 | 1/2015 | Fiering | |
| 2015/0087079 | A1 | 3/2015 | Coffey et al. | |
| 2015/0108056 | A1 | 4/2015 | Charest et al. | |
| 2016/0041163 | A1 | 2/2016 | Ding et al. | |

FOREIGN PATENT DOCUMENTS

| | | | | |
|---|---|---|---|---|
| JP | 2004-239904 | A | 8/2004 | |
| JP | 2014-528067 | A | 10/2014 | |
| WO | WO 2013/036913 | A1 | 3/2013 | |
| WO | WO-2013154946 | A1* | 10/2013 | ....... G01N 33/54306 |
| WO | WO 2017/161350 | A1 | 9/2017 | |

OTHER PUBLICATIONS

Leng et al., "ELISA and Multiplex Technologies for Cytokine Measurement in Inflammation and Aging Research", 2008, The journals of gerontology. Series A, Biological sciences and medical sciences, vol. 63 (8), p. 879-884 (Year: 2008).*

International Search Report and Written Opinion from International Application No. PCT/US2017/23094 mailed Jul. 19, 2017, Application now published as International Publication No. WO2017/161350 on Sep. 21, 2017.

Samborski et al., "Blood diagnostics using sedimentation to extract plasma on a fully integrated point-of-care microfluidic system", Engineering in Life Science, vol. 15, No. 3, pp. 333-339 (2015).

* cited by examiner 5,6A,6B 4A,4B

FIG. 19

MICROFLUIDIC DEVICE AND METHOD

CROSS-REFERENCE TO RELATED APPLICATIONS

This application is a continuation of U.S. application Ser. No. 16/085,997, filed Sep. 17, 2018, issued as U.S. Pat. No. 10,835,898, which is a U.S. National Phase under 35 U.S.C. § 371 of International Application No. PCT/US2017/023094, filed on 17 Mar. 2017, which claims priority under 35 U.S.C. § 119 (e) to U.S. Patent Application Ser. No. 62/310,640 filed Mar. 18, 2016, which are each hereby incorporated by reference in their entirety.

FIELD OF THE INVENTION

The present invention relates to microfluidics, and more particularly to a microfluidic device, system and method for control of fluid flow.

BACKGROUND INFORMATION

Microfluidics relates to the manipulation of small volumes of one or more fluids, e.g., gases and/or liquids. The total volume of fluid may be, e.g., about 250 microliters or less, e.g., about 125 microliters or less, about 75 microliters or less, about 50 microliters or less, or about 25 microliters or less.

The use of microfluidics to determine the presence of at least one target in a liquid sample is known. For example, U.S. Pat. No. 7,824,611 and PCT/US2013/035505, which is incorporated herein by reference in its entirety, discloses immunological assay devices, assay systems and device components having at least two opposing surfaces disposed a capillary distance apart, at least one of which is capable of immobilizing at least one target ligand or a conjugate in an amount related to the presence or amount of target ligand in the sample from a fluid sample in a zone for controlled fluid movement to, through or away the zone. The U.S. Pat. No. 7,824,611 further discloses the use of reagents, such as receptors and conjugates, and biosensors, such as electro-chemical, optical, electro-optical, or acoustic mechanical devices, to determine the presence of one or more targets.

SUMMARY OF THE INVENTION

A microfluidic device generally includes a capillary flow channel disposed within the microfluidic device, the capillary flow channel comprising a proximal opening and a distal opening, a filter pocket disposed at the proximal opening, a mixing well disposed distal to the filter pocket, a dry reagent zone containing a reagent disposed distal to the mixing well, a pinch region disposed distal to the dry reagent zone, and a detection zone disposed distal to the pinch region, wherein the filter pocket, mixing well, dry reagent zone, pinch region and detection zone are in fluidic communication.

In certain aspects, the filter pocket includes a sample inlet having a recess configured to receive a blood volume from a human finger prick, a filter landing and a vent configured to permit air to be displaced upon receiving a liquid sample.

In other aspects, the filter landing includes a raised plateau extending from a distal edge of the filter pocket.

In certain embodiments, a filter pocket can be configured to receive a total volume of blood that is approximately between 25-75 microliters.

In certain embodiments, the filter pocket is configured to receive a total volume of blood that is approximately between 1-10 microliters.

In other embodiments, the filter pocket includes a filter configured to separate red blood cells from plasma of a sample comprising blood.

In certain embodiments, the filter pocket further comprises a catwalk strip disposed for directing the plasma from the sample inlet to the filter landing.

In other embodiments, the mixing well has a bowl shape, having a length, a width, a depth, the well configured to move the filtered liquid sample by capillary action.

In other embodiments, the mixing well has a diameter of approximately 2-6 mm and a depth of 125-225 μm.

In certain aspects, the dry reagent zone contains reagents positioned at the floor of the reagent zone, wherein the reagent zone is configured to reconstitute the dry reagents in the filtered liquid.

In certain aspects, the dry reagent zone contains hydrophobic ink walls having a height that is perpendicular to capillary flow configured to maintain the sample in a hydrophilic region of the reagent zone.

In certain aspects, the dry reagent zone has a width of 1-3 mm, a length of 6-18 mm, and a depth of approximately 50-100 μm.

In one aspect, the pinch region is disposed distal to the reagent and the filtered liquid is moved by capillary action through the pinch region and into the detection zone.

In some aspects, the pinch region is configured with a lobe to increase incubation time for the sample to contact the reagent and move the filtered liquid sample by capillary action, thereby passively controlling fluid flow rate. The pinch can have a length of approximately 10 mm-75 mm, for example 10 mm, 18 mm, 36 mm, 48 mm or 75 mm. The pinch can have a width of approximately 150 μm-250 μm, for example, 150 μm, 215 μm, or 250 μm. The pinch can have a depth of approximately 33 μm to 85 μm, for example 33 μm, 50 μm, 78 μm, or 85 μm.

The flow rate of plasma and blood in the claimed microfluidic device can vary between 1 nl/sec. and 120 nl/sec depending on the location within the capillary flow channel.

In certain aspects, the flow rate of plasma in the filter component mixing well can be between 60-100 nl/sec., such as approximately 80 nl/sec. The flow rate of blood in the filter component mixing well can be between 35-55 nl/sec., such as approximately 40 nl/sec.

The flow rate of plasma in the dry reagent zone can be between 40-80 nl/sec, such as approximately 60 nl/sec. The flow rate of blood in the dry reagent zone can be between 25-70 nl/sec., such as approximately 45 nl/sec.

The flow rate of plasma in the pinch region can be between 2.5-7 nl/sec., such as approximately 4.5 nl/sec. The flow rate of blood in the pinch region can be between 1 nl/sec.-10 nl/sec., such as approximately 3.5 nl/sec.

The flow rate of plasma in the detection zone can be between 7-21 nl/sec., such as approximately 14 nl/sec. The flow rate of blood in the detection zone can be between 6-18 nl/sec., such as approximately 12 nl/sec.

In some aspects, the pinch region has two or more lobes configured to increase incubation time for the sample to contact the reagent and passively control the fluid flow rate.

In some aspects, the pinch region has a width that is ½ the width of the capillary flow channel.

In some aspects, the pinch region has a width that is ¼ the width of the capillary flow channel.

In some embodiments, the pinch region has a width that is ⅙ the width of the capillary flow channel.

In some embodiments, the pinch region has a width that is ¹⁄₁₀ the width of the capillary flow channel.

In some aspects, the pinch region has a depth of at least 50 μm, at least 75 μm, or at least 100 μm.

In some aspects, the detection zone is configured to receive a liquid sample and determine the presence of one or more targets in the liquid sample.

In some aspects, the detection zone contains at least one solid phase capture spot configured to bind a specific analyte, ensure that the liquid passing through the detection zone has sufficiently contacted the capture spot, and provide a signal to measure the response.

In other aspects, the microfluidic device includes two or more solid phase capture spots arranged in a series along the length of the detection zone.

In some aspects, the solid phase capture spot is rounded.

In other aspects, the solid phase capture spot is rectangular.

In some aspects, the solid phase capture spot provides a signal measured by a reader.

In some embodiments, at least one solid phase capture spot serves as a control.

In other aspects, the reader is a scanning fluorimeter.

In other aspects, the signal is processed by software, which correlates the response to a calibrated model and measures the intensity of the response.

In other aspects, the reagent comprises a conjugate comprising a detectable label and a binder for a target.

In certain aspects, the detection zone comprises a binder for the target or a complex of the conjugate and the target.

In other aspects, the microfluidic device, further comprises a waste channel configured to hold excess liquid sample during a wash of the detection zone.

In other aspects, portion of the substrate covers the waste channel and that portion is printed with hydrophobic ink to increase flow rate and decrease wash time.

In other aspects, the waste channel has a length of 3-7 mm, a length of 50-90 mm, and a depth of approximately 25-40 μm.

In other aspects, the channel is disposed between an upper substrate and a lower substrate.

In certain aspects, the lower substrate comprises a first portion having a first depth and a second portion having a second depth that is less than the first depth.

In other aspects, the first depth is at least about 1.5 to 2 times greater than the second depth.

In other aspects, the portion having a first depth is convex and the portion having a second depth is planar.

In other aspects, the microfluidic device further comprises a gap having a height d4 between a lower surface of the filter and an upper surface of the lower substrate, wherein height d increases from a central longitudinal axis of the lower surface of the filter toward the outer perimeter of the portion of the lower substrate having a first depth.

In certain aspects, a portion of the surface of the lower substrate that contacts a central portion of the lower surface of the filter is at a portion of the lower substrate having a first depth.

In other aspects, the height of the gap between the lower surface of the filter and the surface of the lower substrate is constant proceeding from the perimeter of the portion of the substrate having a first depth to the perimeter of the portion of the lower substrate having a second depth.

In other aspects, the microfluidic device further comprises a portion of the substrate having third depth that is less than the second depth.

In other aspects, the third depth is about half of the second depth.

In other aspects, the first depth is defined by the height of the mixing well.

In other aspects, the second depth is defined by the height of the dry reagent zone.

In certain aspects, the third depth is defined by the height of a waste channel disposed distal to the detection zone.

In other aspects, the lower substrate further comprises a fourth depth defined by a plateau, wherein the plateau is disposed in a recess of the filter pocket.

In other aspects, the filter pocket is configured to move the filtered liquid by capillary action along the capillary chamber and into the mixing well of the capillary channel.

In other embodiments, the mixing well is configured to move the filtered liquid by capillary action along the capillary chamber and into the pinch region of the capillary channel.

In certain embodiments, the mixing well, having a greater depth compared to the remainder of the capillary flow channel, is configured to dampen the concentration of filter components and minimize filter component variation between devices.

In certain aspects, the mixing well has a depth of approximately 125-200 μm. In other aspects, the mixing well has a depth of approximately 175 μm, In certain aspects, the microfluidic device further comprises a liquid sample disposed within a proximal portion of the capillary flow channel, the liquid sample comprising a gas-liquid interface disposed within the capillary flow channel proximal to the reagent; and a gas disposed within the capillary flow channel distal to the gas-liquid interface of the liquid sample, the pressure being sufficient to prevent the liquid sample from advancing along the capillary channel toward the reagent.

In certain embodiments, a method for detecting a target in a sample comprises positioning a microfluidic device in an operable relation with a reader for the microfluidic device, the microfluidic device comprising a capillary flow channel comprising a proximal opening and a distal opening, introducing a sample to a filter pocket at the proximal portion of the capillary flow channel, filter pocket separating out a liquid portion of the sample to form a liquid sample, passing the liquid sample through a mixing well to minimize the filter component variation between devices, passing the liquid sample from the mixing well to a dry reagent zone configured to reconstitute dry reagents in the liquid sample, passing the liquid sample from the dry reagent zone to the pinch region configured to increase assay sensitivity by permitting the reagent additional time to incubate with decreased diffusion distance, passing the liquid sample from the pinch region to the detection zone configured to detect the presence of a target, contacting a solid phase capture spot in the detection zone, reading the signal from the solid phase capture spot, and passing the liquid sample from the detection zone to a waste channel, configured to hold excess liquid sample from a wash of the detection zone.

In yet other embodiment, a method for manufacturing a microfluidic device includes positioning a capillary flow channel between an upper and lower substrate, the capillary flow channel comprising a proximal opening and a distal opening, connecting a filter pocket at the proximal portion of the capillary flow channel, the filter pocket configured to separate a liquid portion of the sample to form a liquid sample and advance the liquid sample by capillary flow along only a portion of the capillary flow channel until a gas pressure acting upon a distal gas-liquid interface of the liquid sample prevents the liquid sample from advancing further along the capillary flow channel, positioning a mixing well distal to the filter pocket, the mixing well configured to dampen the concentration of filter components and minimize the filter component variation between devices, positioning a dry reagent zone distal to the mixing well, the dry reagent zone configured to reconstitute dry reagents in the liquid sample, positioning a pinch region distal to the dry reagent zone, the pinch region configured to increase assay sensitivity by permitting the reagent additional time to incubate with decreased diffusion distance, positioning a detection zone distal to the pinch region, the detection zone configured to detect the presence of a target, and positioning a waste channel distal to the detection zone, the waste channel configured to hold excess liquid sample from a wash of the detection zone, wherein the filter pocket, mixing well, dry reagent zone, pinch region and detection zone, are all in fluidic communication.

In yet other embodiments, a method for manufacturing a microfluidic device includes printing a hydrophobic ink on a surface of the upper substrate covering the waste channel, the hydrophobic ink configured to increase flow rate and decrease wash time.

In yet other embodiments, the microfluidic device can also further include a pump in fluidic communication with the distal opening of the capillary flow channel.

In other embodiments, the device can further include a controller configured to operate the pump to decrease the gas pressure in the capillary flow channel by an amount sufficient to cause the liquid sample to advance along the capillary flow channel until at least the gas-liquid interface of the liquid sample contacts the reagent.

In yet other embodiments, the reader is configured to position an optical excitation source and an optical detector in optical communication with the detection zone after moving the pump away from the distal opening of the capillary flow channel.

At least a portion of the surface of the substrate may be convex and/or tapered.

In any of the foregoing filters, a gap between the lower surface of the filter and the surface of the substrate may increase from a central portion of the lower surface of the filter toward the perimeter along at least two opposed directions. In each of the opposed directions, the gap may increase from about 10 microns, e.g., about 15 microns, about 20 microns. In each of the opposed directions, the gap may increase to about 50 microns, to about 75 microns, to 100 microns, to about 200 microns, to about 300 microns, to about 500 microns. In each of the opposed directions, the gap may increase over a lateral distance of at least about 750 microns, at least about 1500 microns, at least about 2000 microns. In each of the opposed directions, the gap may increase over a distance of about 5000 microns or less, about 3000 microns or less, about 2500 microns or less.

In any of the foregoing filters, a portion of the surface of the substrate may contact a central portion of the lower surface of the filter.

In any of the foregoing filters, the filter may have a length and a width, and the portion of the surface of the substrate may contact the central portion of the lower surface of the filter along substantially all of the length of the filter. The length of the filter may be at least about 1.25 times, e.g., at least about 1.5 times, at least about 2.0 times as great as the width of the filter. The length of the filter may be about the same as the width of the filter. The length of the filter may be at least about 2 mm, e.g., at least about 3 mm, e.g., at least about 5 mm, e.g., at least about 7.5 mm, e.g., at least about 10 mm. The length of the filter may be about 15 mm or less, e.g., about 10 mm or less. The width of the filter may be at least about 2 mm, e.g., at least about 2 mm, e.g., at least about 3 mm, e.g., at least about 5 mm, e.g., at least about 7.5 mm, e.g., at least about 10 mm. The width of the filter may be about 15 mm or less, e.g., about 10 mm or less, about 7.5 mm or less, about 5 mm or less.

In any of the foregoing filters in which a portion of the surface of the substrate contacts the lower surface of the filter, the surface of the substrate may contact the lower surface of the filter along less than about half of the width of the filter, e.g., less than about one quarter the width of the filter, e.g., less than about ⅛ of the width of the filter. In any of the foregoing filters in which a portion of the surface of the substrate contacts the lower surface of the filter, the surface of the substrate may contact the lower surface of the filter along at least about half of the length of the filter, e.g., at least about ¾ of the length of the filter, e.g., at least about ⅘ of the length of the filter, at least about ⁹/₁₀ of the length of the filter, e.g., substantially all of a length of the filter. The portion of the substrate that contacts the lower surface of the filter may contact the filter along a length of the filter of at least about 1 mm, at least about 2 mm, at least about 5 mm, at least about 7.5 mm, at least about 10 mm. The portion of the substrate that contacts the lower surface of the filter may contact the filter along a width of the filter of at least about 100 microns, at least about 200 microns, at least about 300 microns, at least about 500 microns. The portion of the substrate that contacts the lower surface of the filter may contact the filter along a width of the filter of about 1000 microns or less, about 750 microns or less, about 500 microns or less.

In any of the foregoing filters, a portion of the surface of the substrate may contact the central portion of the lower surface of the filter along a first dimension of the filter and along a second dimension of the filter and wherein the distance contacted along the first dimension of the filter may be at least about 5 times greater, at least about 7.5 times greater, at least about IO times greater, than along the second dimension of the filter, and wherein the first and second dimensions may be perpendicular.

Any of the foregoing filters may further comprise a capillary flow channel having an opening in fluidic communication with a space between the lower surface of the filter and the surface of the substrate.

Any of the foregoing filters may further comprise a vent in fluidic communication with a space between the lower surface of the filter and the surface of the substrate. The opening of the capillary channel and the vent may be spaced apart by substantially all of a length or width of the filter.

Any of the foregoing filters may comprise pores and a size of the pores may decrease proceeding from the upper surface of the filter toward the lower surface of the filter.

Any of the foregoing filters may be configured to separate red blood cells from a sample of blood and to permit passage of liquid components of the sample of blood.

In any of the foregoing filters, the lower surface of the filter may be convex or tapered along at least one dimension. The lower surface of the filter may be convex or tapered along a dimension perpendicular to a dimension of the filter along which the lower surface of the filter contacts the surface of the substrate.

In any of the foregoing filters, a portion of the surface of the substrate may contact the central portion of the lower surface of the filter along a first dimension of the filter and along a second dimension of the filter and wherein the distance contacted along the first dimension of the filter may be at least about 5 times, e.g., at least about 7.5 times, e.g., at least about 10 times, greater than along the second dimension of the filter, and wherein the first and second dimensions may be perpendicular and further wherein the lower surface of the filter may be convex or tapered along the second dimension of the filter.

In certain embodiments, a method for determining the presence or absence of cardiac troponin in a patient sample includes labeling the troponin, if present, with a label comprising a binding partner for the troponin and a detectable moiety; and detecting troponin in the sample by determining the presence or absence of the label in a handheld assay, wherein detection of the presence of the label indicates the presence of troponin in the sample, wherein the assay has a coefficient of variation of less than about 10% at the $99^{th}$ percentile of a normal reference population.

In other embodiments, a method for determining the presence or absence of cardiac troponin in a patient sample includes labeling the troponin, if present, with a label comprising a binding partner for the troponin and a detectable moiety; and detecting troponin in the sample by determining the presence or absence of the label in a handheld assay, wherein detection of the presence of the label indicates the presence of troponin in the sample, wherein the assay has a limit of quantitation of about 3 µg/mL with a coefficient of variation of less than about 20%.

The troponin can be a cardiac troponin I (cTnI). The troponin can be a cardiac troponin T (cTnT). In certain embodiments, the troponin can be a complex of cTnI and cTnT.

In certain embodiments, the binding partner comprises an antibody specific to the troponin.

In certain embodiments, the patient sample is a blood, serum, or plasma sample. The sample can also be a blood and plasma sample.

In certain embodiments, the presence or absence of the label in the handheld assay can be determined within 20 minutes or less of applying the patient sample to the assay, such as 18 minutes or less, or 16 minutes or less.

In certain embodiments, troponin in the sample can be detected by determining the presence or absence of the label in a handheld assay comprising a microfluidic device.

In other embodiments, the troponin in the sample can be detected by determining the presence or absence of the label in a handheld assay comprising the claimed microfluidic device.

BRIEF DESCRIPTION OF THE DRAWINGS

FIG. 19 indicates an improved performance across a range of different manufacturing batches with the microfluidic device.

DETAILED DESCRIPTION OF THE INVENTION

Figures 1A, 1B:
FIG. 1A is a perspective top view of a microfluidic device.
FIG. 1B is a perspective top view of a microfluidic device further showing a filter pocket.

With reference to FIGS. 1A-7, a microfluidic device 20 is configured to receive a liquid sample for the determination of one or more targets present in the liquid sample. Microfluidic device 20 is formed of a lower substrate 21 and an upper substrate 23 defining there between a capillary flow channel 25 having a proximal opening 27 and a vent 29 disposed adjacent a distal portion 30 of capillary channel 25. A reagent zone 41 and detection zone 43 are disposed within capillary flow channel 25. Microfluidic device 20 further includes a sample introduction port 31 through upper substrate 23. A liquid sample is introduced to microfluidic device via port 31.

The microfluidic device is configured with components designed to passively control the rate of fluid flow through a capillary flow channel.

This application incorporates by reference the subject matter of PCT/US2017/021211 filed on Mar. 7, 2017.

A microfluidic system includes a microfluidic device including a substrate having a lower surface and an upper surface, a capillary flow channel disposed between the upper and lower surface, the capillary flow channel comprising a proximal opening and a distal opening, a filter pocket having a filter landing in fluidic communication with a proximal portion of the capillary flow channel and a filter pocket vent configured to permit air to be displaced upon receiving a liquid sample, a mixing well disposed distal to the filter pocket, a dry reagent zone comprising a reagent on a floor of the reagent zone, wherein the reagent zone is disposed distal to the mixing well, a pinch region disposed distal to the dry reagent zone, and a detection zone disposed distal to the pinch region, wherein the filter pocket, mixing well, dry reagent zone, pinch region and detection zone are in fluidic communication, and a reader configured to receive the capillary flow channel and determine the presence of one or more targets in the liquid sample.

The microfluidic system can further include a liquid sample disposed within a proximal portion of the capillary flow channel, the liquid sample comprising a gas-liquid interface disposed within the capillary flow channel proximal to the reagent; and a gas disposed within the capillary flow channel distal to the gas-liquid interface of the liquid sample, the pressure being sufficient to prevent the liquid sample from advancing along the capillary channel toward the reagent.

A method for detecting a target in a sample can include positioning a microfluidic device in an operable relation with a reader for the microfluidic device, the microfluidic device comprising a capillary flow channel comprising a proximal opening and a distal opening; introducing a sample to a filter pocket at the proximal portion of the capillary flow channel, filter pocket separating out a liquid portion of the sample to form a liquid sample and advancing the liquid sample by capillary flow along only a portion of the capillary flow channel until a gas pressure acting upon a distal gas-liquid interface of the liquid sample prevents the liquid sample from advancing further along the capillary flow channel; passing the liquid sample through a mixing well to minimize the filter component variation between devices; passing the liquid sample from the mixing well to a dry reagent zone configured to reconstitute dry reagents in the liquid sample; passing the liquid sample from the dry reagent zone to the pinch region configured to increase assay sensitivity by permitting the reagent additional time to incubate with decreased diffusion distance; passing the liquid sample from the pinch region to the detection zone configured to detect the presence of a target; and passing the liquid sample from the detection zone to a waste channel, configured to hold excess liquid sample from a wash of the detection zone.

A method for manufacturing a microfluidic device can include positioning a capillary flow channel within a substrate, the capillary flow channel comprising a proximal opening and a distal opening; connecting a filter pocket at the proximal portion of the capillary flow channel, the filter pocket configured to separate a liquid portion of the sample to form a liquid sample and advance the liquid sample by capillary flow along only a portion of the capillary flow channel until a gas pressure acting upon a distal gas-liquid interface of the liquid sample prevents the liquid sample from advancing further along the capillary flow channel; positioning a mixing well distal to the filter pocket, the mixing well configured to dampen the concentration of filter components and minimize the filter component variation between devices; positioning a dry reagent zone distal to the mixing well, the dry reagent zone configured to reconstitute dry reagents in the liquid sample; positioning a pinch region distal to the dry reagent zone, the pinch region configured to increase assay sensitivity by permitting the reagent additional time to incubate with decreased diffusion distance; positioning a detection zone distal to the pinch region, the detection zone configured to detect the presence of a target; and positioning a waste channel distal to the detection zone, the waste channel configured to hold excess liquid sample from a wash of the detection zone, wherein the filter pocket, mixing well, dry reagent zone, pinch region and detection zone, are all in fluidic communication.

A method for manufacturing a microfluidic device can also include printing a hydrophobic ink on a surface of the substrate covering the waste channel, the hydrophobic ink configured to increase flow rate and decrease wash time.

The device, system, or method may employ, for example, immunology (such as through the use of antibodies) and/or electrochemistry to determine the presence of the one or more targets. The method can also include: introducing the liquid sample to a proximal portion of a capillary flow channel; advancing the liquid sample at a first flow rate toward a distal portion of the capillary flow channel until at least a distal gas-liquid interface of the liquid sample contacts a conjugate disposed in dry form within the capillary flow channel, the conjugate comprising a binding agent having an affinity for the target; subsequently, by increasing a gas pressure differential between a proximal gas-liquid interface of the liquid sample and the distal gas-liquid interface of the liquid sample, advancing the liquid sample at a second flow rate toward the distal portion of the capillary flow channel until at least the distal gas-liquid interface contacts a detection zone within the capillary flow channel, the detection zone comprising a second binding agent having an affinity for a complex comprising the conjugate and the target, the second flow rate being slower than the first flow rate; and subsequently, by increasing the gas pressure differential between the proximal and distal gas-liquid interfaces of the liquid sample, advancing the liquid sample a third flow rate toward the distal portion of the capillary flow channel until at least a majority of conjugate is bound to the second binding agent and/or been advanced beyond the detection zone toward the distal end of the capillary flow channel.

Figure 7:
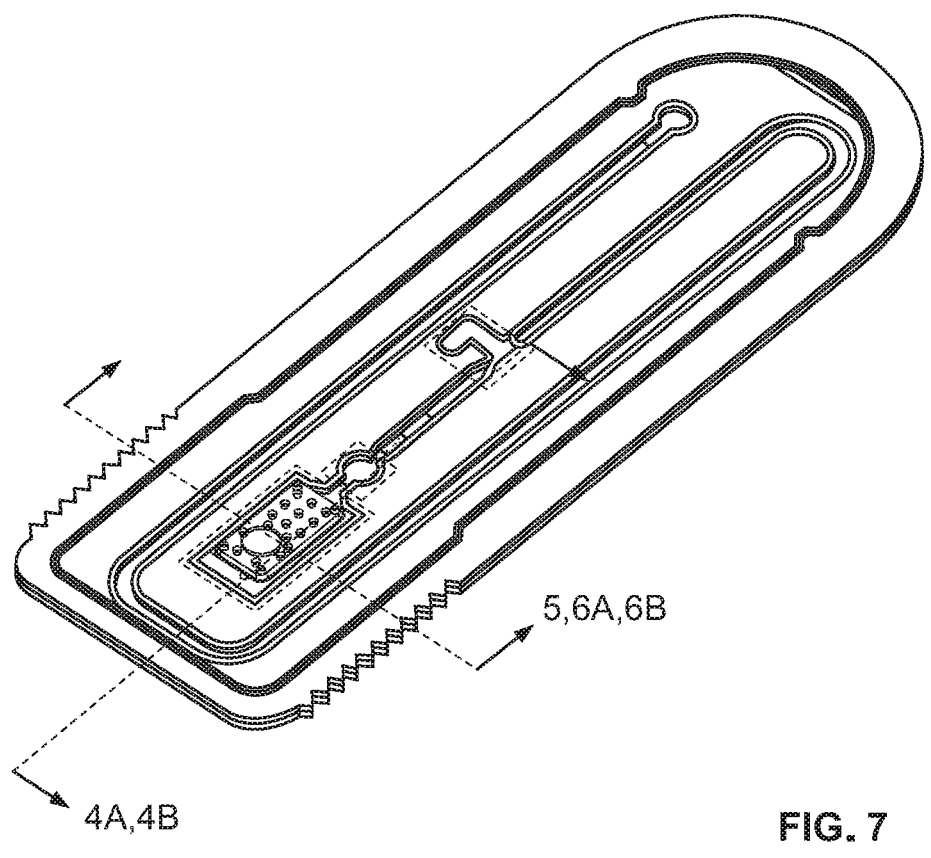
FIG. 7 is identical with FIG. 1A except for showing the cross-sections of FIGS. 4A, 4B, 5, 6A, and 6B.
Figure 8:
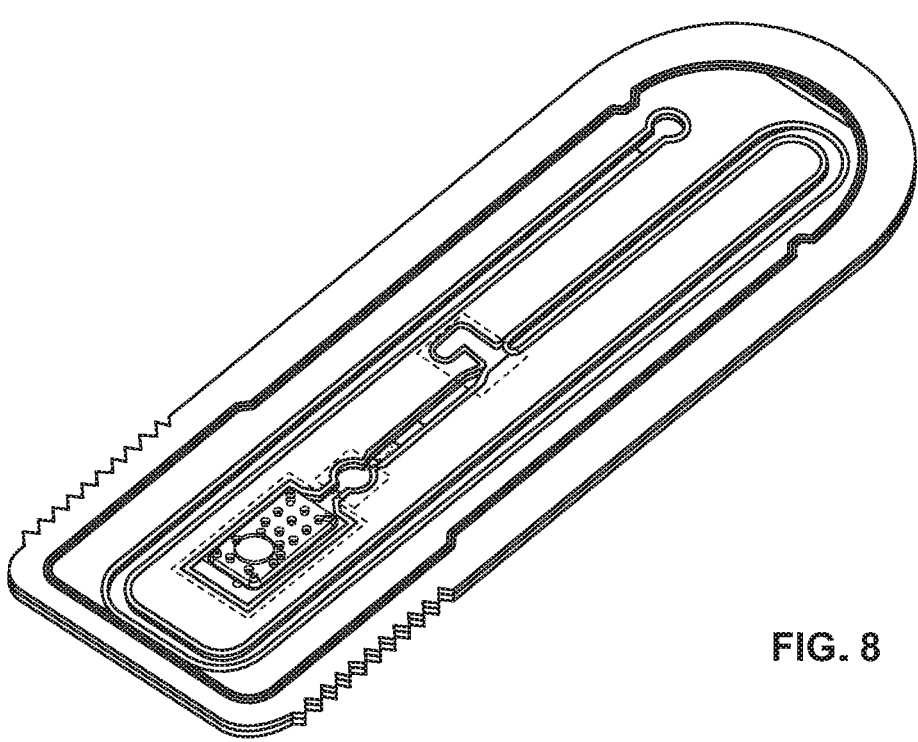
FIG. 8 is a perspective top view of the microfluidic device of FIG. 1A with a sample filter removed.

Referring to FIG. 1A, a microfluidic device can include a mixing well 210 and pinch region 230. The microfluidic device can have a lower substrate that includes a filter pocket 201 comprising inlet or port 31, a filter landing 202 (FIG. 3B) in fluidic communication with a proximal portion of the capillary flow channel 25, and a filter pocket vent 49 (FIG. 14) configured to permit air to be displaced upon receiving a liquid sample. FIG. 7 indicates cross-sections of FIG. 1A, which are depicted in more detail in FIGS. 4A and 4B, and FIGS. 5, 6A and 6B. FIG. 8 is a perspective top view of the microfluidic device of FIG. 1A with a sample filter removed.

Filter Pocket

Figure 3A:
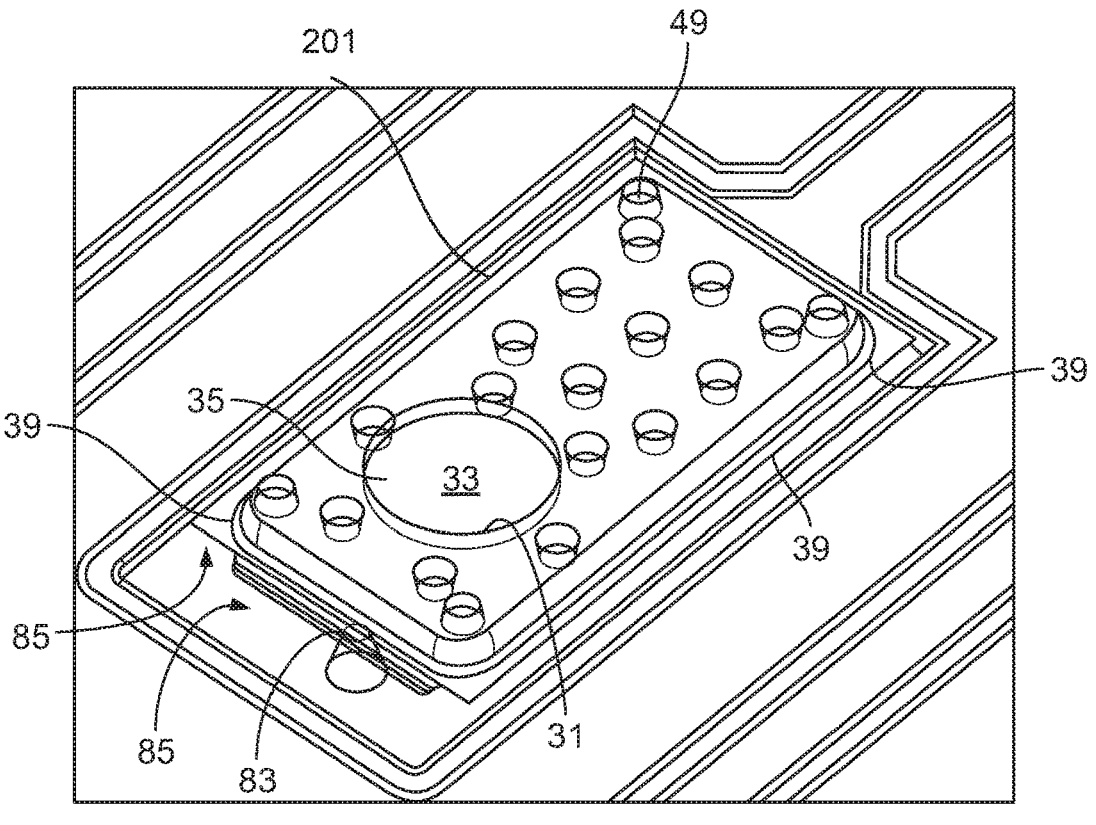
FIG. 3A is a further close-up view of the filter pocket of FIG. 1A
Figure 3B:
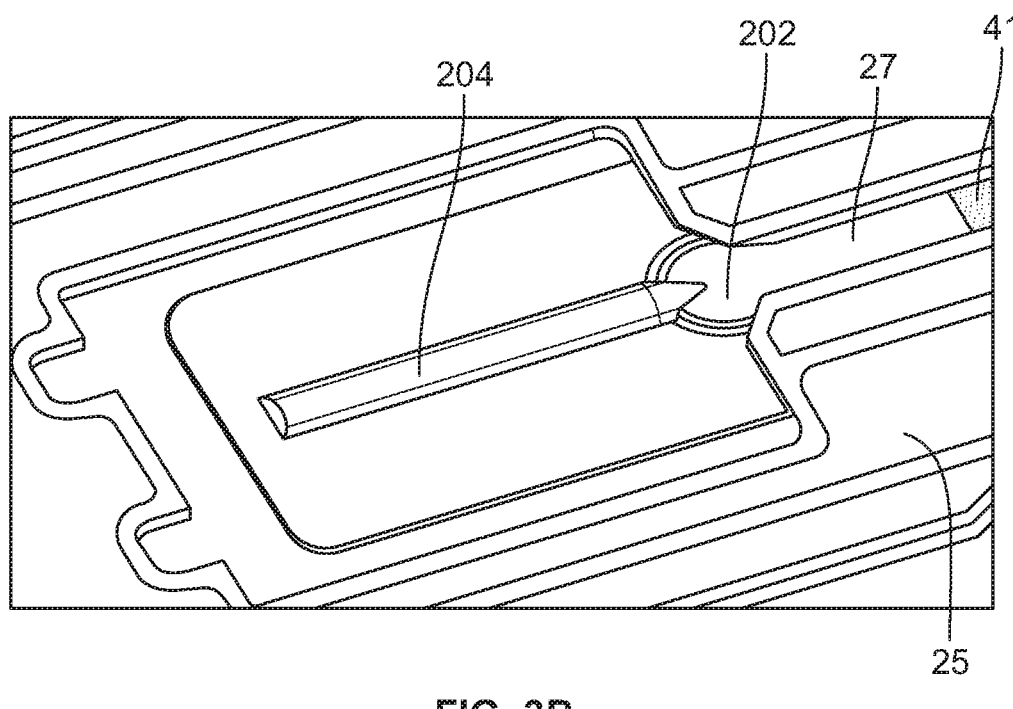
FIG. 3B is a further close-up view of the filter pocket of FIG. 1A from the perspective of FIGS. 1A and 2 showing a catwalk and filter landing.

Referring to FIGS. 3A-3B, a microfluidic device can include a filter 33 at sample inlet 31. The filter pocket can further include a catwalk 204 and filter landing 202. The catwalk can be an elongated strip having a length that extends parallel to a length of the filter pocket, and having a width that is broader at a proximal end than at a distal end. The distal end is tapered to direct a collected sample to a mixing well and diagnostic lane or detection zone based on microfluidic principles of passive fluid control techniques such as capillary forces.

Figure 2:
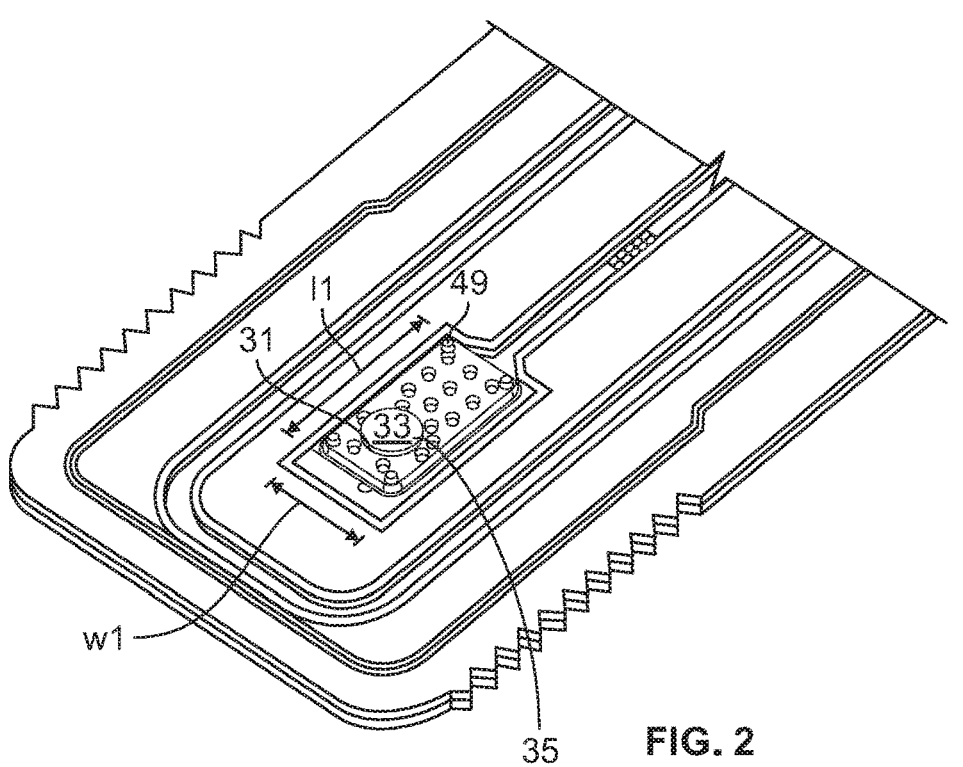
FIG. 2 is a close-up view of the microfluidic device of FIG. 1A from the perspective of FIG. 1A

Referring to FIG. 3B, which is a close-up view of the microfluidic device of FIG. 1A from the perspective of FIGS. 3A and 2, the filter pocket can further include a catwalk 204 and filter landing 202.

The filter landing 202 is in fluidic communication with a proximal portion of the capillary flow channel and a filter pocket vent configured to permit air to be displaced upon receiving a liquid sample. The filter landing is structured as a raised plateau extending from a distal edge of the filter pocket.

Figure 4A:
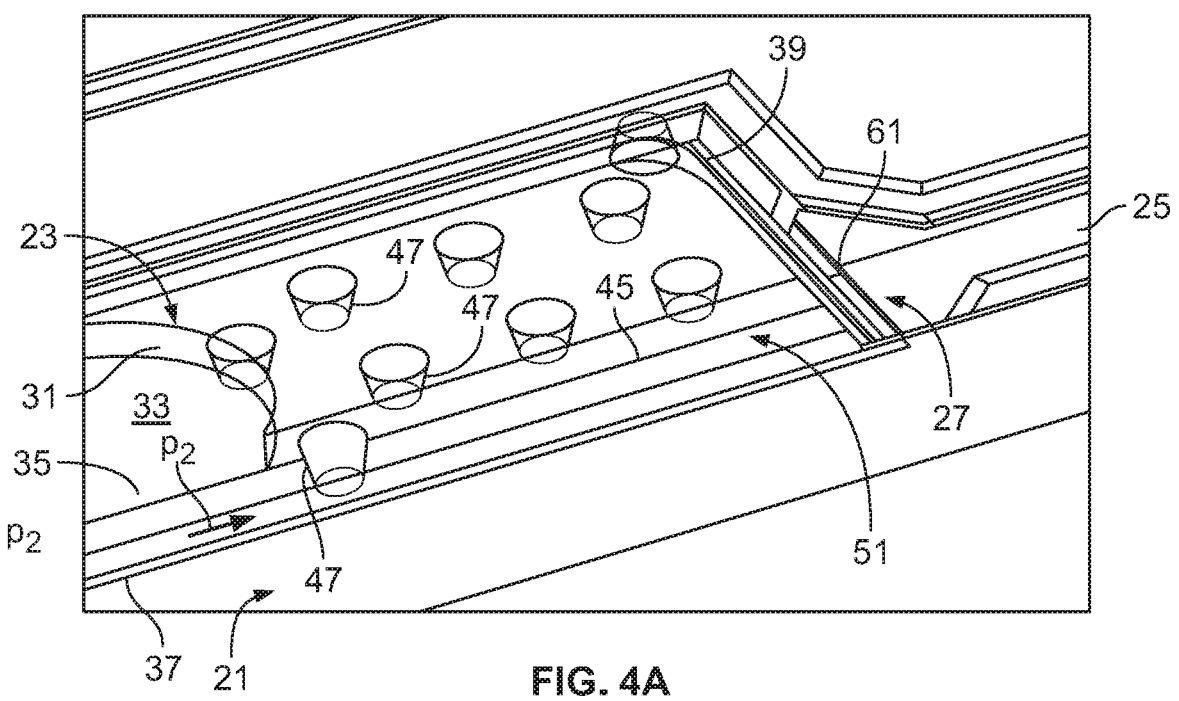
FIG. 4A is a close-up perspective cross-sectional view through filter pocket of the microfluidic device of FIG. 1A taken along the cross section shown in FIG. 7.

The filter pocket includes a filter an upper surface 35 and a lower surface 37 disposed between lower and upper substrates 21 and 23 (FIG. 4A). The filter's upper surface 35 is typically configured to receive a liquid sample, e.g., blood or urine, comprising particulates, e.g., cells, such as red or white blood cells, by application to upper surface 35 and to prepare a filtered liquid sample with a reduced number such particulates, e.g., essentially free of such particulates, through lower surface 37. In certain embodiments, the filter pocket is designed and dimensioned to capture small sample volumes, for example, associated with the blood volume of a finger prick. This allows the device to be used at a point of care, or even with an end user in certain situations.

In certain embodiments, the filter includes pores 47 having a diameter or size that decreases proceeding from upper surface 35 toward lower surface 37 (FIG. 4A). The pores can be positioned in a regular pattern or alternatively, in a more random configuration. The size variation of the pores is typically configured so that the particulates in a liquid sample applied to upper surface 35 pass into an interior of filter 33 but do not pass through second lower surface 37 of filter 33. The filter may also be used to deliver one or more reagents to the liquid sample such as one or more buffers, one or more anti-coagulants, one or more salts, one or more stabilizers, one or more protein blockers protein, or combination of one or more such reagents. Additional or alternative reagents include reagents that reduce hemolysis of red blood cells in blood samples and reagents that improve the wettability of the filter with respect to aqueous samples.

The filter pocket of the microfluidic device can be configured to move the filtered liquid by capillary action along the capillary chamber and into the mixing well of the capillary channel. Similarly, the mixing well can be configured to move the filtered liquid by capillary action along the capillary chamber and into the pinch region of the capillary channel. The mixing well can have a greater depth compared to the remainder of the capillary flow channel and thereby be configured to dampen the concentration of filter components and minimize filter component variation between devices. The mixing well can have a depth of approximately 125-225 μm, such as approximately 125, 150, 175, 200 or 225 μm.

In certain embodiments, the filter pocket includes sample inlet port 31 configured to receive a blood volume from a human finger prick. The filter pocket can be configured to receive a total volume of blood that is about 75 microliters, 50 microliters, 30 microliters, 20 microliters, 15 microliters, or 10 microliters. In some embodiments, a filter pocket comprises a filter configured to filter red blood cells from the blood plasma a sample comprising blood. In other embodiments, the filter landing 202 includes a raised plateau extending from a distal edge of the filter pocket. In other embodiments, the filter pocket further comprises a catwalk strip disposed for directing the plasma from the sample inlet to the filter landing.

Mixing Well

The mixing well 210 is disposed distal to the filter pocket and proximal to a dry reagent zone. The mixing well can have a rounded shape and a proximal opening and a distal opening, with the proximal opening in communication with the filter pocket and the distal opening in communication with the dry reagent zone. The dry reagent zone is, in turn, in communication with a pinch region. The mixing well can be have a length, a width, a height, and a perimeter defining a cavity, the width decreasing from a central portion of the mixing zone toward the perimeter along at least two opposed directions, thereby configured to move the filtered liquid sample by capillary action into the mixing well of the capillary channel. In certain embodiments, the mixing well can be free of chemical additives, and in other embodiments, the mixing well can contain a cocktail of chemical additives.

In certain embodiments, the mixing well has a length, a width, a height, and a perimeter defining a cavity; the width decreasing from a central portion of the mixing zone toward the perimeter along at least two opposed directions, thereby configured to move the filtered liquid sample by capillary action into the mixing well of the capillary channel. In certain aspects, the flow rate of plasma can be between 60-100 nl/sec in the filter component mixing well, such as approximately 80 nl/sec. The flow rate of blood in the filter component mixing well can be between 35-55 nl/sec., such as approximately 40 nl/sec.

Dry Reagent Zone

Figures 1C, 1D:
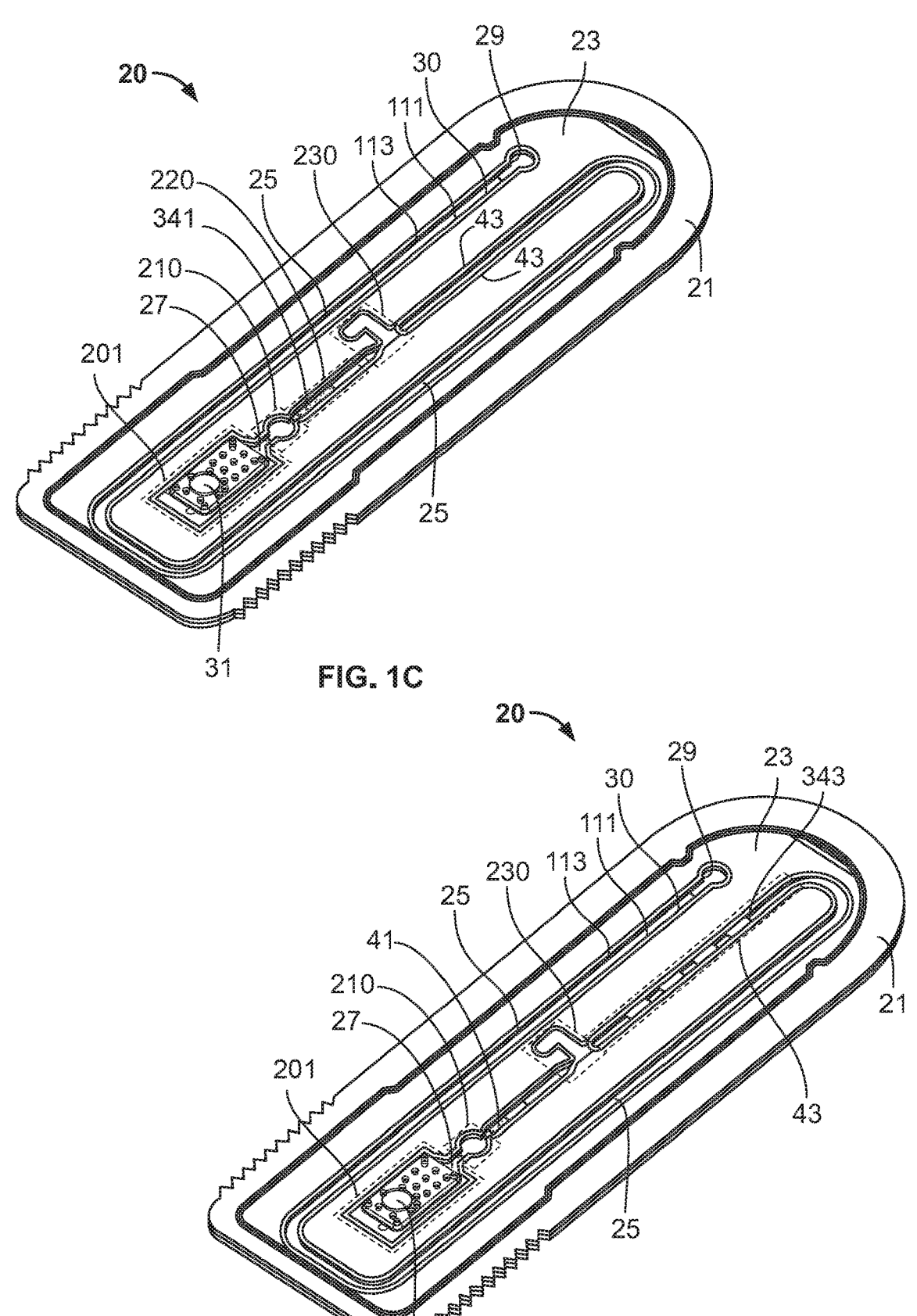
FIG. 1C is a perspective top view of a microfluidic device further showing a dry reagent zone.
FIG. 1D is a perspective top view of a microfluidic device further showing a diagnostic lane or detection zone.

Referring to FIG. 1C, a microfluidic device can further include a dry reagent zone 220. This zone includes one or more reagents 341 that facilitate detection of one or more targets in a liquid sample. Exemplary reagents and techniques for depositing such reagents are described in U.S. Pat. No. 7,824,611, which is incorporated herein by reference.

The dry reagent zone 220 refers to the portion of the channel where a reagent 341 is dried down and reconstituted in the sample. Reagent and target (if any) combine and/or react with dry reagent zone, e.g., by binding a detectable label to a binding agent present in the reagent zone. After a period of time sufficient to permit the filtered liquid and reagent to react and/or combine, capillary action draws the liquid further along capillary channel 25 through the pinch region. In other embodiments, a pump may be also actuated to cause the filtered liquid to move. The flow rate of plasma in the dry reagent zone can be between 40-80 nl/sec, such as approximately 60 nl/sec. The flow rate of blood in the dry reagent zone can be between 25-70 nl/sec., such as approximately 45 nl/sec.

Pinch Region

The pinch region 230 refers to a portion of the channel that curves or is lobed in a direction that is substantially perpendicular to the length of the microfluidic device. It is a fluid resistance feature used to increase assay sensitivity and allow the target analyte and reagent to incubate with decreased diffusion distance. It is dimensioned to optimize fluid flow and control. The width and height of the channel need to be large enough to promote capillary movement without stopping the flow. The length of the pinch region can be structured as a function of increased residence time and restrict fluid movement. In preferred embodiments, residence time is enhanced without impeding fluid flow and decreasing the accuracy of the test. The pinch region 230 is disposed distal to the reagent zone and the filtered liquid sample is moved by capillary action through the pinch region and into the detection zone. The pinch region is configured to move the filtered liquid sample by capillary action thereby passively controlling the fluid flow rate. The pinch region is configured with at least one lobe to increase incubation time for the sample to contact the reagent and passively control the fluid flow rate and increase assay sensitivity. In other embodiments, the pinch region can have two or more lobes configured to increase incubation time for the sample to contact the reagent and passively control the fluid flow rate and increase assay sensitivity. The pinch region thereby achieves a more uniform distribution of liquid along its length, without being affected by temperature of atmospheric pressure.

In certain embodiments, the microfluidic device can have a pinch region 230 in which the channel in the pinch region has a width that is less than the width of the capillary flow channel. For example, the width can be ½, ¼, ⅙, or ¹⁄₁₀ the width of the capillary flow channel, or less. The flow rate of blood in the pinch region can be between 1 nl/sec.-10 nl/sec., such as approximately 3.5 nl/sec. The pinch can have a length of approximately 10 mm-75 mm, for example 10 mm, 18 mm, 36 mm, 48 mm or 75 mm. The pinch can have a width of approximately 150 μm-250 μm, for example, 150 μm, 215 μm, or 250 μm. The pinch can have a depth of approximately 33 μm to 85 μm, for example 33 μm, 50 μm, 78 μm, or 85 μm. In certain embodiments, the flow rate of liquid in the pinch region is 1.0 nl/sec to 10 nl/sec, and in certain embodiments, the flow rate is at least 2.5 nl/sec, at least 3.5 nl/sec, at least 4.5 nl/sec, at least 5.5 nl/sec. The flow rate of plasma in the pinch region can be between 2.5-7 nl/sec., such as approximately 4.5 nl/sec. The flow rate of blood in the pinch region can be between 1 nl/sec.-10 nl/sec., such as approximately 3.5 nl/sec.

Detection Zone

A detection zone is a diagnostic lane of the channel that is disposed distal to the pinch region and generally parallel to the length of the microfluidic device. The filter pocket, mixing well, dry reagent zone, pinch region and detection zone are in fluidic communication within the microfluidic device.

In some embodiments, the detection zone is configured to receive a liquid sample and determine the presence of one or more targets in the liquid sample. The detection zone can include a reagent that comprises a conjugate comprising a detectable label and a binder for a target. The detection zone can also include a binder for the target or a complex of the conjugate and the target. The flow rate of plasma in the detection zone can be between 7-21 nl/sec., such as approximately 14 nl/sec. The flow rate of blood in the detection zone can be between 6-18 nl/sec., such as approximately 12 nl/sec.

The microfluidic device includes a channel 25, which has a width of about 900 microns, between reagent zone 41 and distal portion 30. In certain embodiments, the width of channel 25 is at least about 500 microns, at least about 750 microns, at least about 850 microns. The width of channel 25 may be about 2500 microns or less, about 2100 microns or less, or about 1750 microns or less.

In certain embodiments, the lower substrate comprises a portion having a first depth and a portion having a second depth that is less than the first depth. In some embodiments, the first depth is at least about 2 times, at least about 1.8 times, or at least about 1.5 times greater than the second depth. For example, the first depth can be 175 μm, and the second depth can be 75 μm. In some embodiments, the portion having a first depth is convex or bowl-shaped and the portion having a second depth is planar or flat. The first depth can refer to the depth of the mixing bowl, which the second depth can refer to the depth of the dry reagent zone.

Referring to FIG. 1D, the microfluidic device includes a diagnostic lane or detection zone 43. The detection zone can contain solid phase capture spots 343 (see FIG. 15) that can be rectangular or rounded in shape, and which are arranged in a series along the length of the detection zone. One or more of the solid phase spots can be controls to ensure that the liquid passing through the detection has sufficiently contacted the testing spots, and provides a chance for corrective action if signal response is deemed too high or too low. One or more of the solid phase spots can be designed to bind specific analytes or markers that provide a signal, such as a fluorescent signal for example. The solid phase spots can be measured by a reader, such as a scanning fluorimeter. Software can correlate the fluorimeter's read to a certain calibration model or algorithm and coverts fluorimeter units to a concentration value as a measure of signal response.

Reagent and target (if any) combine and/or react with detection zone, e.g., by binding a detectable label to a binding agent present in detection zone 43. Capillary action draws the filtered liquid further along capillary channel until substantially all reagents from the reagent zone that has not bound to a target has moved distal of detection zone 43 along capillary channel.

Figures 1E, 1F:
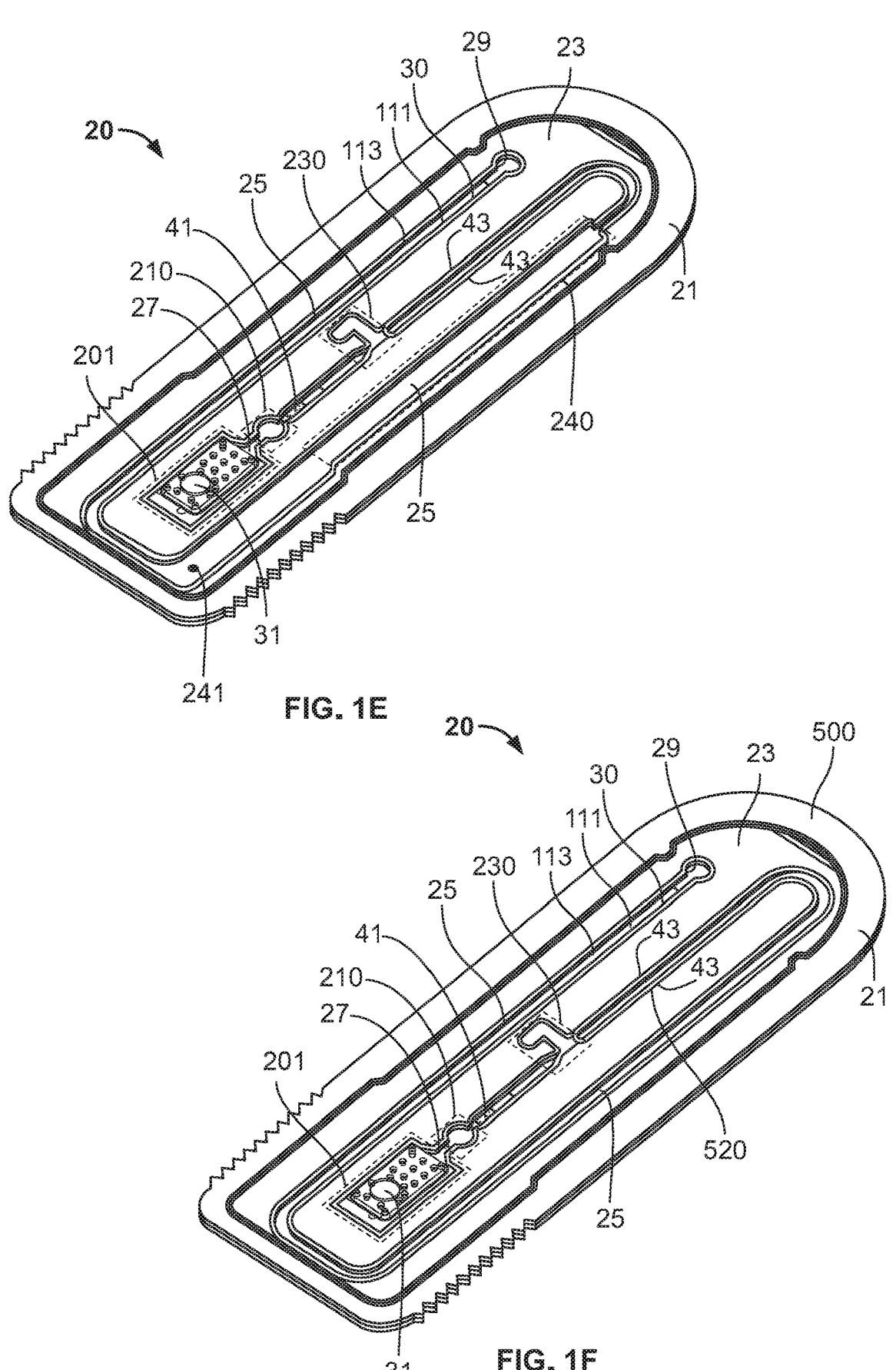
FIG. 1E is a perspective top view of a microfluidic device further showing a waste channel.
FIG. 1F is a perspective top view of a microfluidic device further showing a temperature variable fluorescence.

In a further embodiment, referring to FIG. 1F, a microfluidic device 20 further comprises a composition that displays a temperature variable fluorescence. For example, a first temperature sensor 500 comprises an amount of a composition that has a temperature variable fluorescence and is disposed on the distal surface of microfluidic device 20, and a second temperature sensor 520 comprises an amount of a composition that has a temperature variable fluorescence provided as a micro particle that may either be fixedly attached to an inner surface capillary flow channel 25 in the region of detection zone 43, or may be provided within reagent zone 41, such that when a sample is applied to microfluidic device 20, temperature sensor 520 is reconstituted in liquid sample and migrates along capillary flow channel 25.

First temperature sensor 500 is interrogated by the optics of an optical reader when microfluidic device 20 is first inserted into the optical reader. The measured fluorescence of temperature sensor 500 is compared against a stored profile to provide a first temperature value of microfluidic device 20. Second temperature sensor 520 is subsequently interrogated by the optics of the optical reader to provide a second temperature value of microfluidic device 20. The first temperature value and second temperature value may then be incorporated into an analytical algorithm used to determine presence or amount of a target in the liquid sample. Signals recorded at detection zone 43 which relate to target that has been captured may vary as a function of assay temperature. For example, when detection zone 43 comprises an immunoassay, wherein a surface immobilised antibody is provided to capture a soluble ligand, the kinetics of any binding interaction will vary as a function of temperature. Such effects may include changes in the binding rate as well as the dissociation rate, which may be further affected by changes in the viscosity of the supporting liquid.

Temperature sensors may be implemented using any suitable fluorescent material which displays a temperature dependent fluorescence. Examples of such material include, but are not limited to, quantum dots, rhodamine red, tetramethylrhodamine and dyes from the carbocyanide group. Such dyes typically display a difference in the magnitude of the emission peak as a function of temperature. It is thus possible to develop a calibration profile that permits the determination of assay temperature based on the fluorescence intensity of the respective first and second temperature sensors (500, 520).

Through combined determination of the temperature immediately external to microfluidic device 20 as well as of the fluid sample within, improvements in assay performance can be achieved, based on temperature compensation algorithms that take into consideration the effects of temperature on immunoassay behavior, including the variation in measurement signal that results from greater or lesser capture of target ligand at the sensor surface.

In a further embodiment, microfluidic device 20 is configured to determine the presence or amount of a cardiac troponin I in a sample of blood obtained from a subject. With reference to FIG. 1B, microfluidic device 20 comprises a first agent capable of specifically binding with cardiac troponin I (cTnI) which is conjugated with a fluorescent particle disposed within dry reagent zone 220. Detection zone 43 comprises a second agent capable of specifically binding with cTnI, which agent is immobilised within detection zone 43, such that it serves to capture and localise any cardiac troponin I present within a sample applied to microfluidic device 20. The first and second agents can both bind cTnI simultaneously, such that when cTnI is present within a sample applied to microfluidic device 20, a complex is formed within detection zone 43, which results in accumulation of fluorescent particles within detection zone 43 in an amount proportional to the amount of cTnI present within the sample. Additional details regarding the specific binding and sensitivity of similar assays are set forth, e.g., in U.S. application Ser. No. 13/297,894, U.S. Pat. No. 8,114,612, and WO 96/33415, which are incorporated by reference herein.

The improvements described above in reference to microfluidic device 20, discussed in reference to FIGS. 1A-E, have resulted in an improvement in the clinical performance of the assay for cTnI. In one example, to comply with National Institute for Health and Care Excellence (NICE) guidelines for high-sensitivity troponin tests, the assay is required to achieve strict performance criteria as set forth, e.g. in diagnostic guidance 15 provided by NICE ("Myocardial infarction (acute): Early rule out using high-sensitivity troponin tests (Elecsys Troponin T high-sensitive, ARCHITECT STAT High Sensitive Troponin-I and AccuTnI+3 assays)"), which is incorporated by reference herein.

In particular, the assay is expected to achieve greater than 80% clinical sensitivity and specificity. During evaluation, the assay was shown to have at the $99^{th}$ percentile (at 41 ng/L) a sensitivity of 84.8% and a specificity of 89.5%; at the $97.5^{th}$ percentile (at 14 ng/L) a sensitivity of 91.1% and a specificity of 81.5%.

The assay is expected to achieve less than 10% coefficient of variation at the $99^{th}$ percentile (the upper limit of the reference population) of normals (41 ng/L). During evaluation the assay demonstrated a limit of quantification (LOQ)* of: 3 ng/L at 15% CV (plasma) and 4 ng/L at 15% CV (whole blood). Reference points* 25 ng/L-5.4-8.9% CV, 15 ng/L-4-9.5% CV (whole blood), 25 ng/L-4.3-6.4% CV, 15 ng/L-5.2-8.6% CV (plasma). *based on samples from 25 subjects tested across 6 manufacturing batches of assay devices.

The assay was also shown to demonstrate less than 5% bias difference when comparing measurements made in blood with those made in plasma. The assay also demonstrated an allowable total error of less than 20% around the $99^{th}$ percentile (the expected performance was to be 95% of results within +/−20% of expected value).

Figure 17:
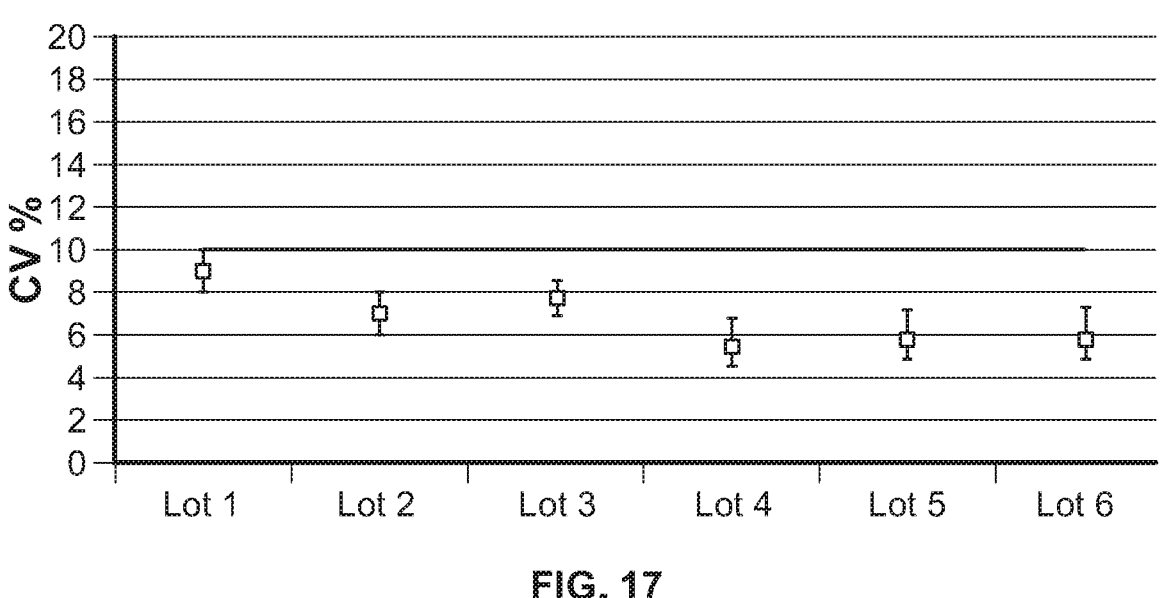
FIG. 17 indicates an improved assay performance across a range of different manufacturing batches with the microfluidic device.
Figure 18:
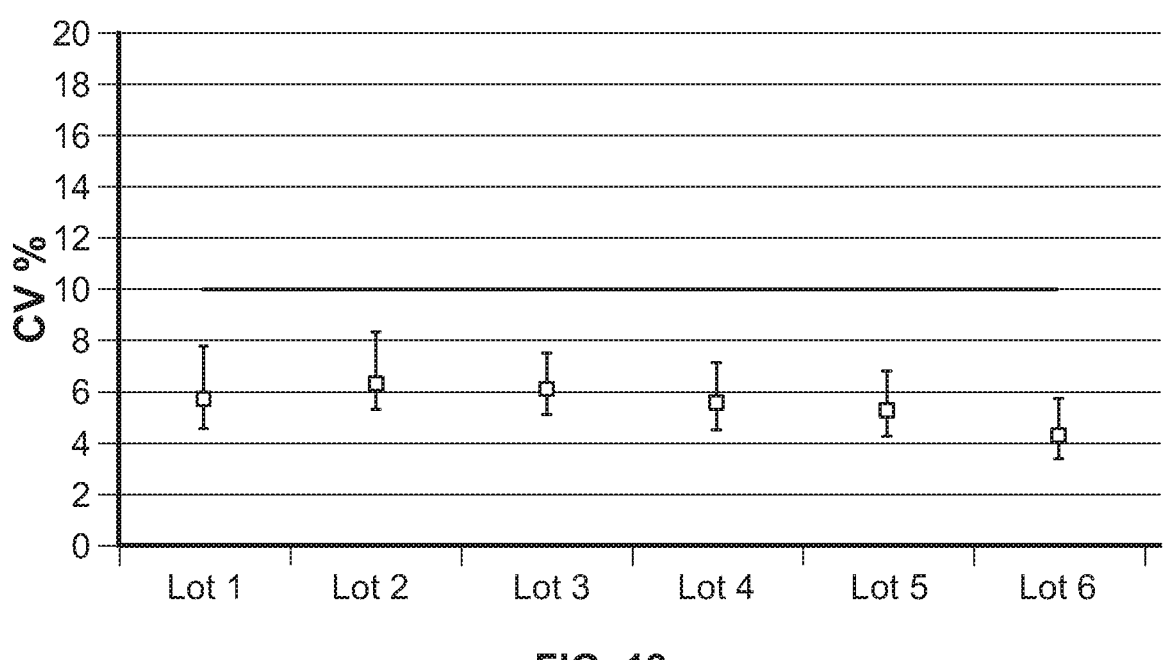
FIG. 18 indicates an improved performance across a range of different manufacturing batches with the microfluidic device.
Figure 19:
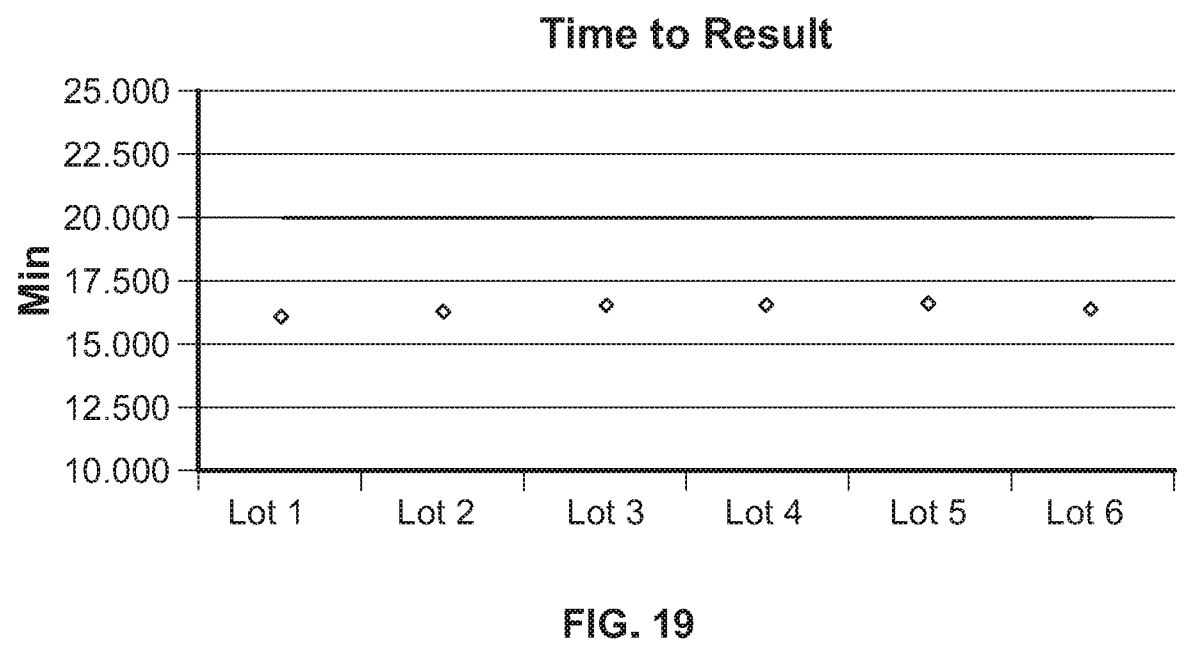

A further general improvement resulted in a total time to result of 16 minutes (from an industry benchmark of 20 minutes), as indicated in FIG. 19. The industry standard is indicated by the bold horizontal line at 20 mins, and the assay performance data is shown by the diamond shaped points.

eferring to FIGS. 17 and 18, these results indicate general assay performance across a range of six different manufacturing batches. FIG. 17 represents assay precision determined at 25 ng/L cTnI spiked into whole blood. The industry standard is indicated by the bold horizontal line at 10% CV. The assay performance data is indicated in by the square shaped points. FIG. 18 represents assay precision determined at 25 ng/L cTnI spiked into plasma. The industry standard is indicated by the bold horizontal line at 10% CV. The assay performance data is indicated in by the square shaped points. In each case, as shown in the graphs, the mean variance ranges from about 4% to about 8%, well below the 10% threshold that was specified within manufacturing parameters. Similar industry standards are set forth, e.g., in expert consensus documents that set forth the criteria for myocardial infarction. See, e.g., vol. 126, issue 16, pages 2020-2035 of *Circulation* (Oct. 16, 2012), also incorporated by reference herein.

Figure 15:
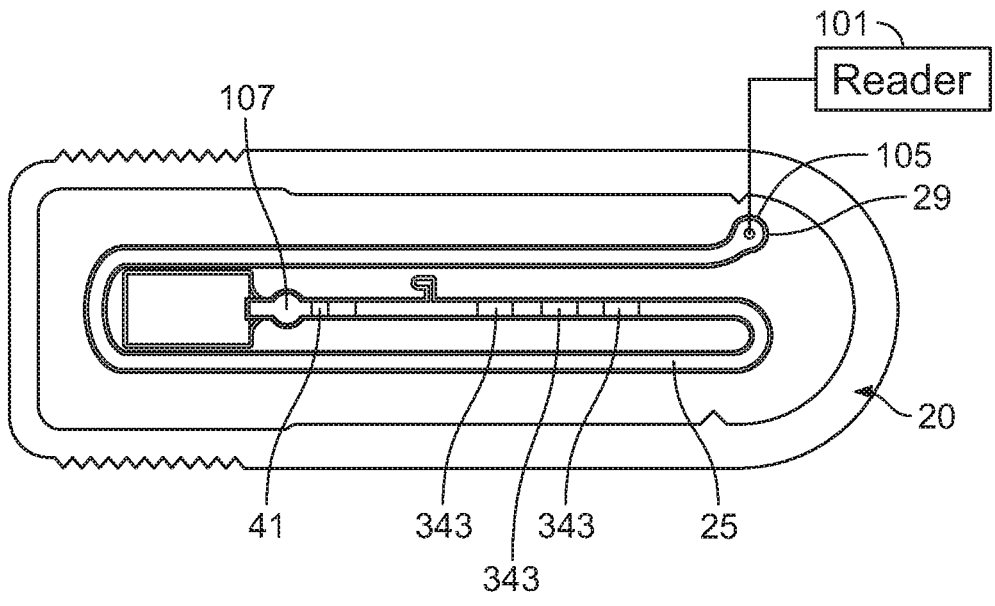
FIG. 15 is a top view of the microfluidic device of FIG. 1A in a first state following the introduction of a liquid sample but with the top substrate having been removed as in FIG. 5.
Figure 16:
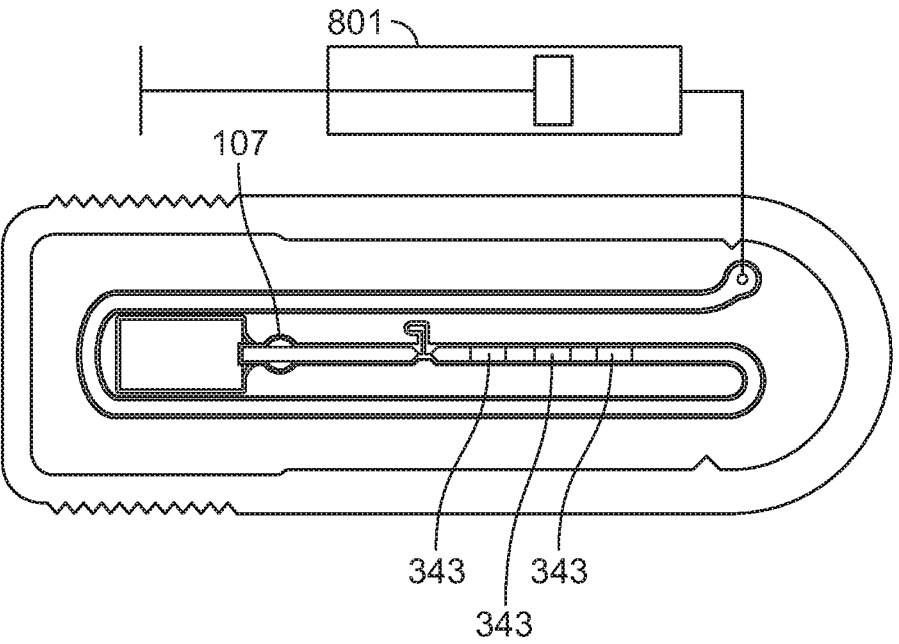
FIG. 16 is a top view of the microfluidic device of FIG. 1A in a first state following the introduction of a liquid sample but with the top substrate having been removed as in FIG. 5 and further showing a pump.

In certain embodiments, such as FIGS. 15-16, a microfluidic device can further include a reader and pump. After a period of time sufficient to permit the filtered liquid and reagent to react and/or combine with certain solid phase spots 343, a reader can actuate syringe pump 801 to increase the volume of the enclosed gas by an amount sufficient to decrease the gas pressure acting on distal gas-liquid interface 107.

In certain embodiments, the detection zone is shaped as channel having opposed walls along a length of a channel, the top of the walls being flanked by a UV scribe line. The walls of the detection zone can be coated with hydrophobic ink, the ink acting as a time gate or fluid stop, and wherein the capillary draw is a function of the thickness of the ink.

The UV scribe line can be created by a process for joining a first substrate to a second substrate, for example, by irradiating a portion of a first substrate with a laser beam having a first wavelength and intensity sufficient to increase the absorbance of the first substrate to light having a second, different wavelength. This is described, for example in WO/2013/163433, which is incorporated by reference herein. For example, the laser beam may carbonize at least a portion of the irradiated portion of the first substrate. The carbonized portion of the first substrate typically has a higher absorbance to light than non-irradiated portions of the first substrate. A second substrate is then placed in contact with the irradiated portion of the first substrate. With the first and second substrates in such contact, the irradiated portion of the first substrate is irradiated with a second laser having a second wavelength, different to the first wavelength; with a sufficient intensity to heat and, preferably melt, the irradiated portion of the first substrate. Because the absorbance of irradiated portions of the first substrate is higher than that of non-irradiated portions of the first substrate, the second laser beam efficiently heats (and preferably melts) the previously irradiated portions of the first substrate causing the first and second substrates to become joined together, without substantially affecting portions of the substrate not previously exposed to the first wavelength laser. In embodiments, the joined first and second substrates form at least a portion of a microfluidic device.

Waste Channel

Referring to FIG. 1E, a microfluidic device further can further include a waste channel 240. The waste channel is shaped to hold excess liquid sample from a wash of the detection zone, wherein the filter pocket, mixing well, dry reagent zone, pinch region and detection zone, are all in fluidic communication. In certain embodiments, the waste channel can be covered by a surface coated with the hydrophobic ink configured to increase flow rate and decrease wash time.

Referring to FIG. 2, filter 33 has a length $l_1$ and a width $w_1$ (FIG. 2) sufficient to provide an area to accommodate a desired amount of sample applied to upper surface 35 thereof. For example, length $l_1$ may be at least about 2.5 mm, at least about 5 mm, at least about 7.5 mm. Length $l_1$ may be about 25 mm or less, about 20 mm or less, about 15 mm or less, about 10 mm or less. Width $w_1$ may be at least about 2.5 mm, at least about 3.5 mm, at least about 5 mm. Width $w_1$ may be about 17.5 mm or less, about 12.5 mm or less, about 10 mm or less, about 7.5 mm or less.

Figure 13:
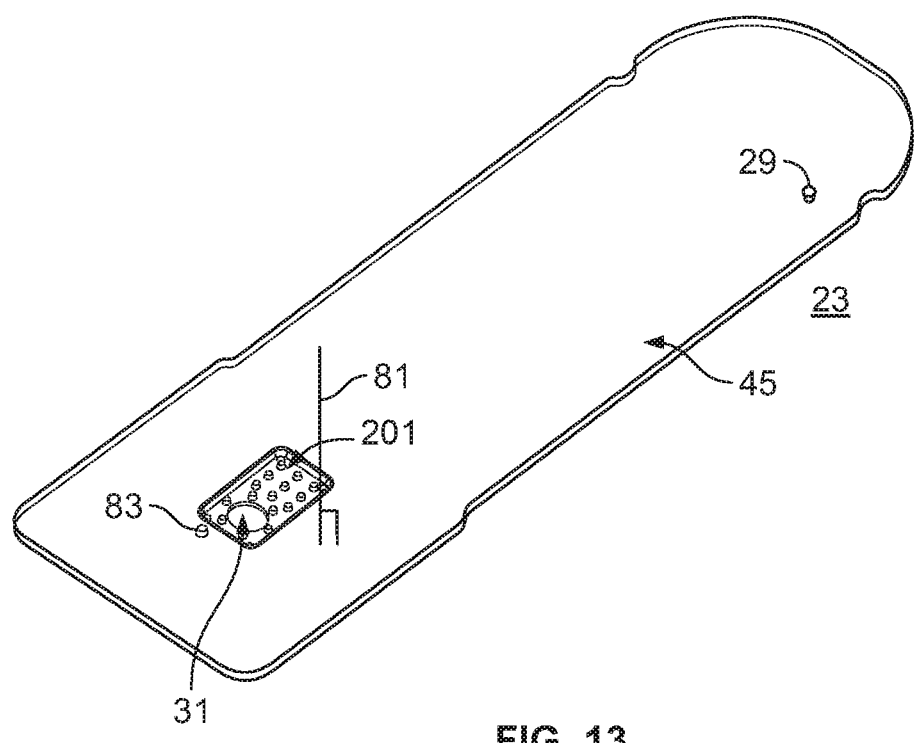
FIG. 13 is a perspective view of an underside of the upper substrate of the microfluidic device of FIG. 1.

Filter 33 is typically secured with respect to upper substrate 23. For example, a perimeter portion 39 (FIG. 3A) of upper surface 35 of filter 33 may be attached, e.g., by heat staking, laser welding, or via an adhesive, to a lower surface of upper substrate 23. In the embodiment of FIGS. 1-3, filter 33 is not attached to lower substrate 21, although such attachment may be used. Also with reference to FIGS. 13 and 14, a portion of filter 33, e.g., an upper portion of upper surface 35 disposed interior to perimeter 39, is accommodated within a detection zone 43 of a lower surface 45 of upper substrate 23. Filter pocket 201 includes a plurality of projections 46 that project outwards from lower surface 45 of substrate 23 for a distance dl. Projections 46 contact upper surface 35 of filter 33 forming a cavity 51 having a height about the same as, e.g., the same as, distance dl. Typically, distance dl is sufficient to permit a gas and/or liquid sample to flow between upper surface 35 of filter 33 and lower surface 45 of substrate 23. In embodiments, dl may be at least about 5 microns, at least about 10 microns, at least about 15, microns, or at least about 25 microns. In embodiments, d1 is about 1000 microns or less, about 250 microns or less, about 175 microns or less, about 125 microns or less, or about 100 microns or less.

Figure 14:
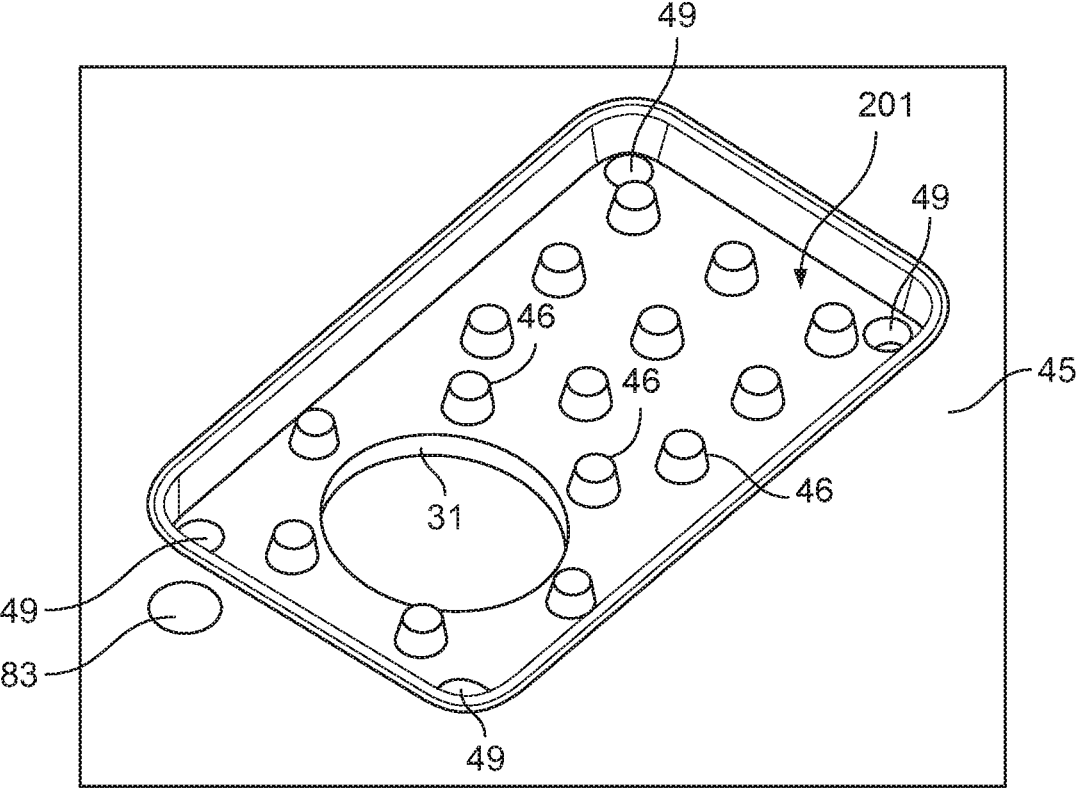
FIG. 14 is a close-up view of the underside of the upper substrate shown in FIG. 13.

Referring to FIGS. 3A-3B and FIG. 14, filter pocket 201 also includes a plurality of vents 49 that permit gas to pass between filter pocket 201 and the ambient atmosphere (e.g., the atmosphere generally surrounding the microfluidic device) without passing through port 31. In use, liquid sample applied to filter 33 through port 31 travels laterally across upper surface 35 of filter 33 in cavity 51 between upper surface 35 and lower surface 45 of upper substrate 23 while gas displaced by the advancing liquid escapes filter pocket 201 via vents 49. Thus, sample applied to port 31 will contact an area of upper surface 35 of filter 33 that is larger than an area of port 31. This permits a more efficient use of filter 33 than if liquid applied to port 31 contacted an area of upper surface 35 limited to the area of port 31. In embodiments, a ratio of an area of upper surface 35 of filter 33 to an area of port 31 is at least about 1.5, at least about 2, or at least about 2.5. In embodiments, the ratio of the area of upper surface 35 of filter 33 to the area of port 31 is about 10 or less, about 7.5 or less, or about 5 or less. Typically, liquid sample applied to filter 33 through port 31 will contact at least about 50%, at least about 75%, at least about 80%, at least about 90%, or more of the area of upper surface 35 of filter 33.

Referring to FIGS. 4A, 4B, 5, 6A, 6B, and 10, an upper surface 53 (FIG. 6B) of lower substrate 21 (FIG. 4A, FIG. 6B) defines a filter contact surface 55 (FIG. 6A) comprising a ridge 57 (FIG. 10) and a distal portion 59. A lower surface 37 of filter 33 (FIG. 5) contacts lower substrate 21 only at filter contact surface 55 (although in some embodiments, lower surface 37 may contact lower substrate 21 at locations other than filter contact surface 55).

Figure 6A:
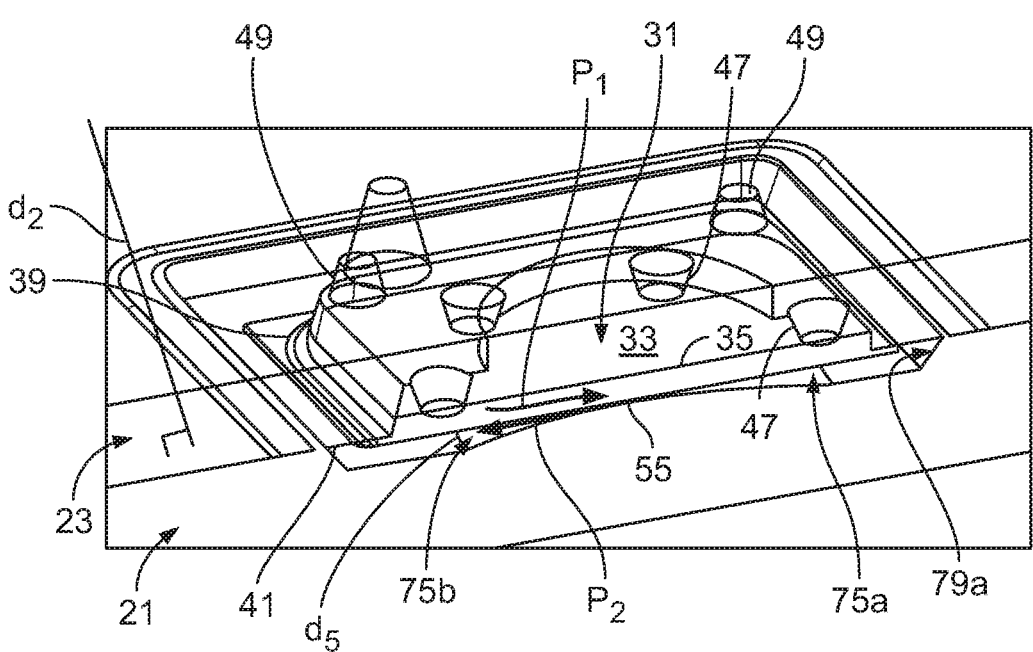
FIG. 6A is a close-up perspective cross-sectional view through a filter pocket of the microfluidic device of FIG. 1A taken along the cross section shown in FIG. 7.
Figure 6B:
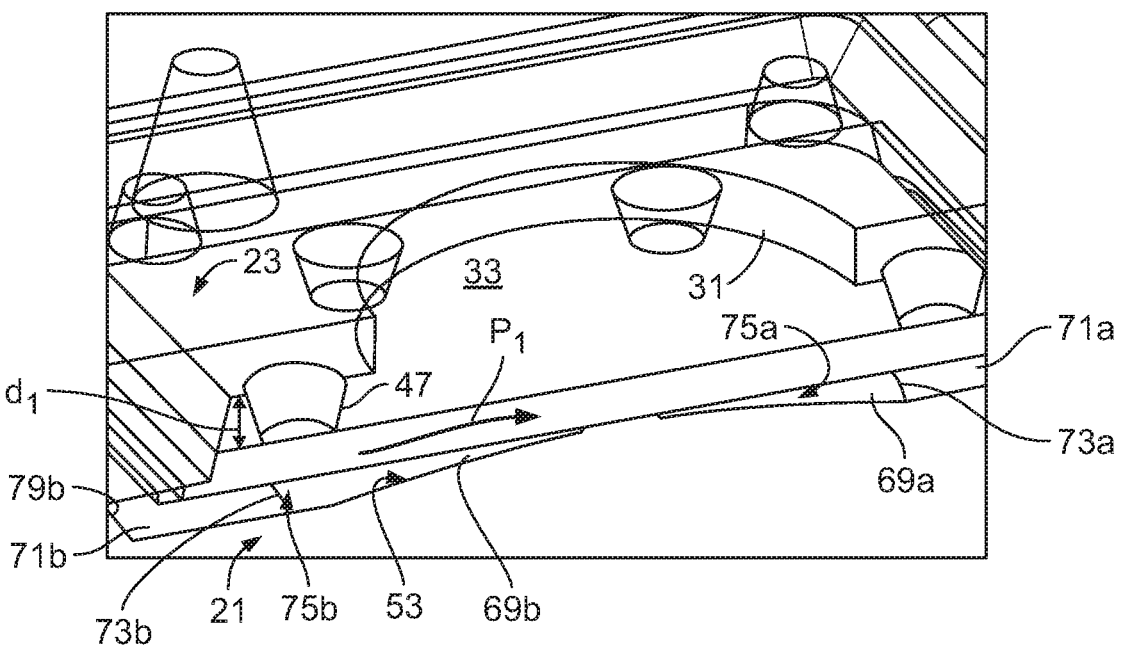
FIG. 6B is a further close-up perspective cross-sectional view through a filter pocket of the microfluidic device of FIG. 1A taken along the cross section shown in FIG. 7 from the perspective of FIG. 6A

In embodiments, filter 33 permits liquid sample passing from upper surface 35 to lower surface 37 to move laterally within filter 33, e.g., along a path P2 (FIGS. 4A and 4B) and/or a path P1 (FIGS. 6A and 6B). Such lateral movement permits liquid sample applied to filter 33 at upper surface 35 within port 31 to exit lower surface 37 of filter 33 at locations laterally spaced apart from filter pocket 201.

Filter contact surface 55 contacts lower surface 37 of filter 33 only at locations of lower surface 37 that are disposed inwardly from perimeter 39 of filter. A distance between perimeter 39 and the nearest contact point of contact surface 55 may be at least about 250 microns, at least about 375 microns, at least about 500 microns, at least about 750 microns, or at least about 1 mm.

Figure 10:
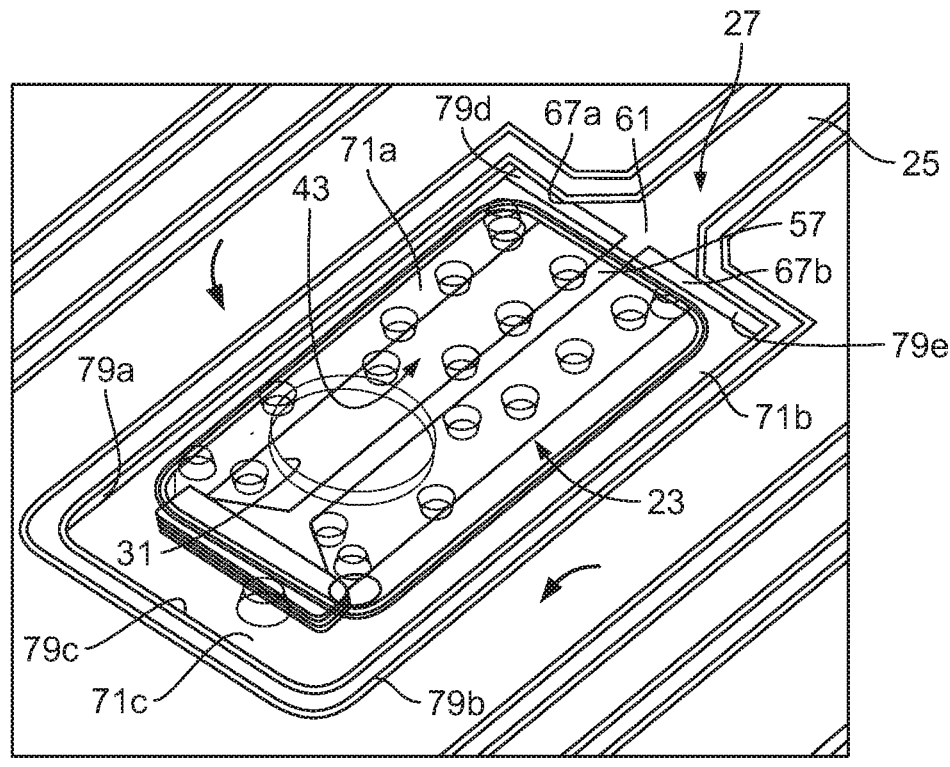
FIG. 10 is a further close-up view of the microfluidic device of FIG. 1A with the sample filter removed and depicting the hydrophobic portions of the device.

Ridge 57 (FIG. 4B) extends proximally from a proximal floor 61 of proximal opening 27 of capillary channel 25 to distal portion 59 of filter contact surface 55 (FIG. 10). In embodiments, ridge 57 of filter contact surface 55 (FIG. 6A) contacts lower surface 37 of filter 33 at one or more locations spaced apart along at least about 50%, at least about 70%, at least about 80%, at least about 90%, at least about 95%, e.g., substantially all of length 11 of filter 33. For example, ridge 57 of filter contact surface 55 may contact lower surface 37 of filter 33 continuously (i.e., without gaps) along at least about 50%, at least about 70%, at least about 80%, at least about 90%, at least about 95%, e.g., substantially all of length 11 of filter 33. In embodiments, a length 12 of ridge 57 of filter contact surface 55 is at least about 5 mm, at least about 7.5 mm, at least about 10 mm. Length 12 may be about 25 mm or less, about 20 mm or less, or about 15 mm or less.

In embodiments, ridge 57 of filter contact surface 55 contacts lower surface 37 of filter 33 at one or more locations spaced apart along about 50% or less, about 30% or less, about 25% or less, about 20% or less, about 15% or less, or about 10% or less of width w1 of filter 33. In embodiments, ridge 57 of filter contact surface 55 has a width w2 (FIG. 12) of at least about 100 microns, at least about 200 microns, at least about 300 microns, at least about 500 microns. Width w2 of filter contact surface 55 may be about 1000 microns or less, about 750 microns or less, about 650 microns or less, or about 500 microns or less. In embodiments, length 12 of ridge 57 is at least about 5 times greater, at least about 7.5 times greater, at least about 10 times greater, at least about 15 times greater than width w2 of ridge 57 where length 12 and width w2 are taken along perpendicular dimensions of ridge 57.

Figures 11, 12:
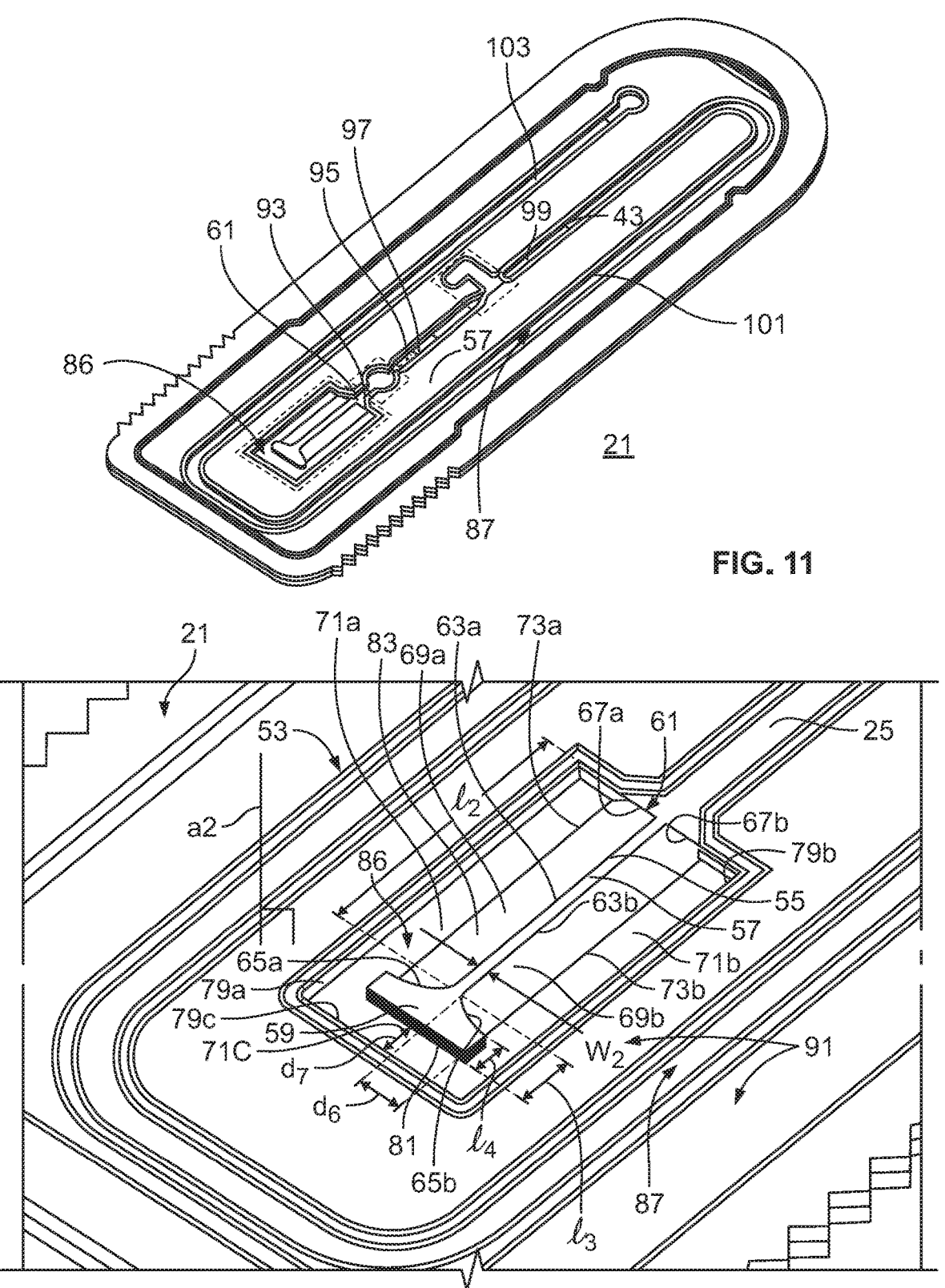
FIG. 11 is a perspective top view of the microfluidic device of FIG. 1A with the sample filter removed and with an upper substrate removed.
FIG. 12 is a close up view of the microfluidic device of FIG. 1A with the sample filter and upper substrate removed as in FIG. 11.

A maximum length 13 of distal portion 59 of filter contact surface 55 is typically less than length 12 of ridge 57 of filter contact surface 55 (FIG. 12). For example, a ratio of 13 and 13 may be about 0.5 or less, about 0.35 or less, about 0.25 or less, about 0.2 or less, or about 17.5 or less. A minimum length 14 of distal portion 59 of filter contact surface 55 is typically less than length 13 (FIG. 12). For example, a ratio of length 14 and 13 may be about 0.95 or less, about 0.9 or less, about 0.8 or less.

Ridge 57 of filter contact surface 55 defines first and second opposed walls 63a, 63b and distal portion 59 of filter contact surface 55 defines first and second distal walls 65a, 65b. Proximal portion 61 of capillary channel 25 defines first and second proximal walls 67a, 67b. Upper surface 53 of lower substrate 21 defines first and second sloping floor portions 69a, 69b and first, second and third hydrophobic floor portions 71a, 71b, 71c. First and second sloping floor portions 69a, 69b and first and second hydrophobic floor portions 71a, 71b are respectively separated by first and second junctions 73a, 73b. A third hydrophobic floor portion 71c is disposed distal to a distal wall 81 extending downward from distal portion 59 of the filter contact surface.

As seen, for example, in FIGS. 10 and 12, peripheral portions of first, second, and third hydrophobic floor portions 71a, 71b, 71c abut peripheral walls 79a, 79b, 79c, 79e that extend upward to define a perimeter of a filter pocket 81 in upper surface 53 of lower substrate 23. Capillary contact surface 55 and first and second proximal floor portions 69a, 69b constitute a projection extending above first, second, and third hydrophobic floor portions 71a, 71b, 71c within filter pocket 81.

Taken together, first and second opposed walls 63a, 63b, first and second distal walls 65a, 65b, first and second proximal walls 67a, 67b, first and second junctions 73a, 73b, first and second sloping floor portions 69a, 690b, and portions of lower surface 37 above first and second sloping floor portions 69a, 690b, and portions of lower surface 37 below first and second sloping floor portions 69a, 690b define respective sample cavities 75a, 75b.

Figure 4B:
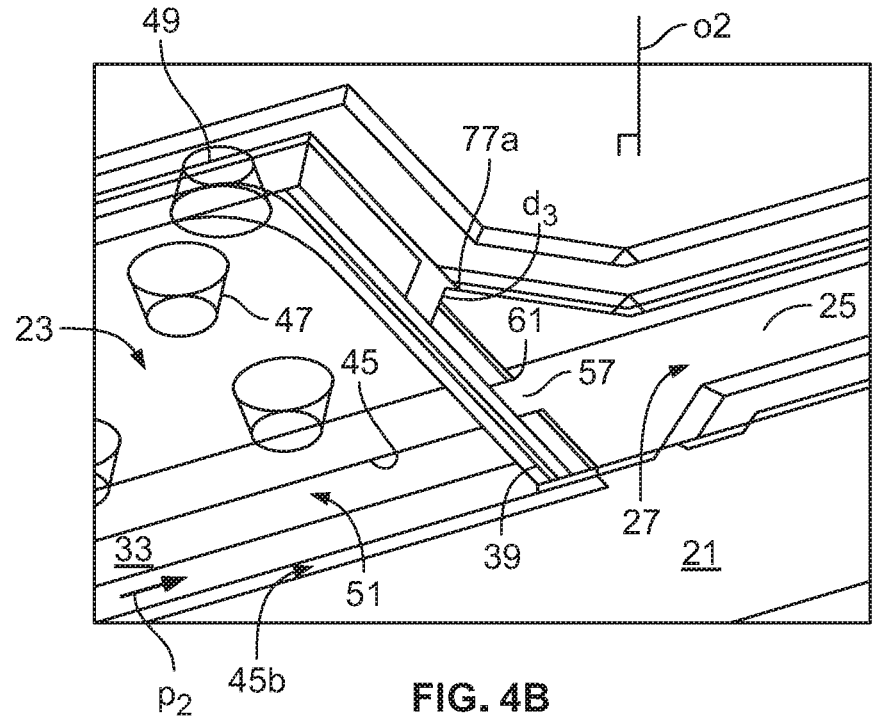
FIG. 4B is a further close-up perspective cross-sectional view through a filter pocket of the microfluidic device of FIG. 1A taken along the cross section shown in FIG. 7 from the perspective of FIG. 4A
Figure 5:
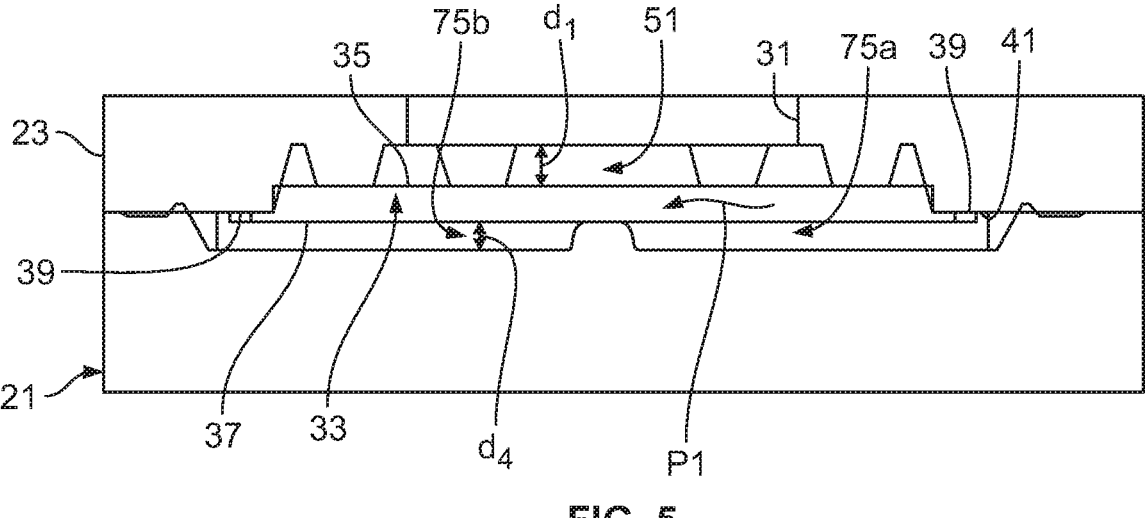
FIG. 5 is a cross-sectional view through the filter pocket of the microfluidic device of FIG. 1 taken along the cross section shown in FIG. 7.

With reference to FIG. 4B, FIG. 6A and FIG. 12, sample cavities 75a, 75b are spaced apart from, e.g., disposed below, a level of floor 61 of capillary channel 25 along an axis a2 oriented normal to lower substrate 21. In embodiments, at least about 50%, at least about 75%, at least about 85%, at least about 95%, essentially all of a volume of cavities 75a, 75b is disposed below floor 61 of the proximal portion of capillary channel 25 along axis a2. In embodiments, at least about 50%, at least about 75%, at least about 85%, at least about 95%, or essentially all of an active area of lower surface 37 of filter 33 is disposed at or below floor 61 of the proximal portion of capillary channel 25 along axis a2. In embodiments, at least about 50%, at least about 75%, at least about 85%, at least about 95%, essentially all of a volume of cavities 75a, 75b is disposed at or at a greater distance along axis a2 from an upper surface of upper substrate 23 than floor 61 of the proximal portion of capillary channel 25. In embodiments, at least about 50%, at least about 75%, at least about 85%, at least about 95%, or essentially all of an active area of lower surface 37 of filter 33 is disposed at or at a greater distance along axis a2 from an upper surface of upper substrate 23 than floor 61 of the proximal portion of capillary channel 25. An active area of filter 33 is the area through which filtered liquid emerges during use.

Taken together, first, second, and third hydrophobic floor portions 71a, 71b, 71c, portions of lower surface 37 of filter 33 above and first, second, and third hydrophobic floor portions 71a, 71b, 71c peripheral walls 79a, 79b, 79c, 79e define a peripheral cavity 85 in gaseous communication with sample cavities 75a, 75b. A vent 83 permits gas to pass between on the one hand active cavities 75a, 75b and peripheral cavity 85 and, on the other hand, the ambient atmosphere (e.g., the atmosphere generally surrounding the microfluidic device) without passing through filter 33. Vent 83 is disposed distal of active cavities 75a, 75b.

A height d2 of first and second opposed walls 63a, 63b is typically at least about 10 microns, at least about 20 microns, at least about 30 microns, at least about 50 microns, at least about 75 microns, at least about 100 microns, or at least about 150 microns. Height d2 may be about 175 microns or less, about 125 microns or less, about 100 microns or less, about 75 microns or less, or about 50 microns or less. Typically, height d2 of first and second opposed walls 63a, 63b is about the same as, e.g., the same, as the height of first and second proximal walls 67a, 67b immediately adjacent ridge 57 and proximal portion 61 of capillary channel 25. In embodiments, height d2 is zero so that first and second sloping floor portions 69a, 69b slope downwards from ridge 57 of filter contact surface 55.

Because first and second sloping floor portions 69a, 69b slope away from lower surface 37 of filter 33 proceeding laterally away from ridge 57, the height of first and second proximal walls 67a, 67b increases from a minimum immediately adjacent ridge 57 and proximal portion 61 of capillary channel 25 to a maximum height d3 at lateral portions 77a, 77b of first and second proximal walls 67a, 67b. Height d3 of lateral portions 77a, 77b of first and second proximal walls 67a, 67b is typically at least about 30 microns, at least about 50 microns, at least about 75 microns, at least about 100 microns, at least about 150 microns, at least about 200 microns, or at least about 250 microns. Height d3 may be about 500 microns or less, about 350 microns or less, about 300 microns or less, about 275 microns or less, or about 225 microns or less. First and second sloping floor portions 69a, 69b have a convex shape in at least one dimension, e.g., are cylindrically convex about an axis extending between first and second proximal walls 67a, 67b and first and second distal walls 65a, 65b. In embodiments, first and second sloping floor portions 69a, 69b are planar or arcuate.

A height of first and second distal walls 65a, 65b, i.e., the distance between distal portion 59 of filter contact surface 55 and first and second sloping floor portions 69a, 69b, is typically about the same as the height of first and second proximal walls 67a, 67b, which, as discussed above, increases from a minimum immediately adjacent ridge 57 and proximal portion 61 of capillary channel 25 to a maximum height d3 at lateral portions 77a, 77b of first and second proximal walls 67a, 67b.

A height d4 of a gap between first and second junctions 73a, 73b of upper surface 53 of lower substrate 21 and lower surface 37 of filter 33 (FIG. 5) is typically at least as large as, e.g., larger than, height d3 at lateral portions 77a, 77b of first and second proximal walls 67a, 67b.

Figure 9:
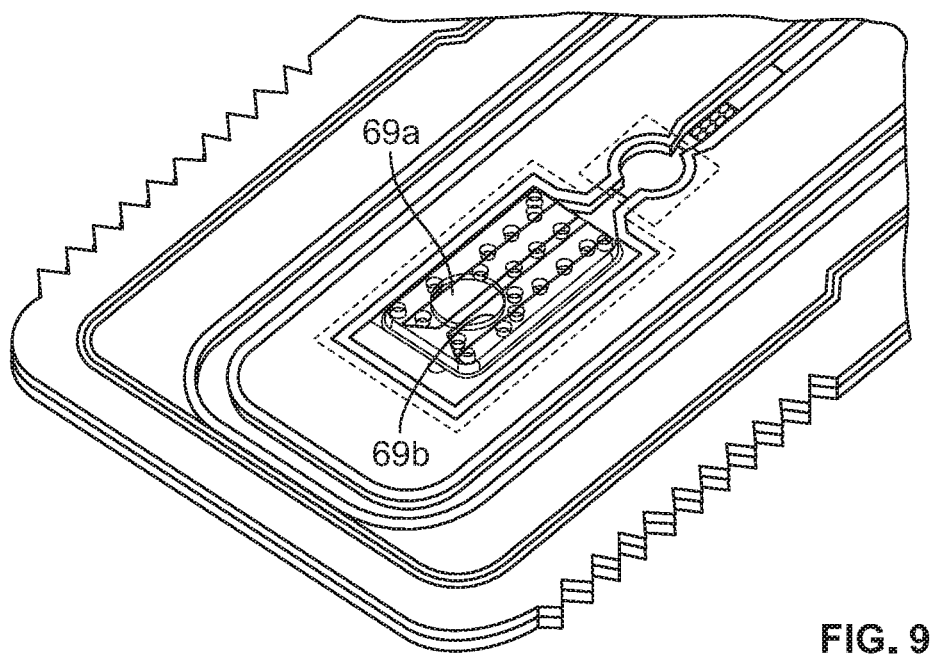
FIG. 9 is a close-up view of the microfluidic device of FIG. 1A showing the height d4 of a gap between first and second junctions of upper surface of the lower substrate and lower surface of the filter.

Referring to FIG. 9, Height d4 is typically constant (but may also vary) is selected to optimize fluid management and is typically at least about 30 microns, at least about 50 microns, at least about 75 microns, at least about 100 microns, at least about 150 microns, at least about 200 microns, or at least about 250 microns. Height d4 may be about 600 microns or less, about 400 microns or less, about 350 microns or less, about 300 microns or less, or about 275 microns or less. A height d5 between first and second hydrophobic floor portions 71a, 71b of upper surface 53 of lower substrate 21 and lower surface 37 of filter 33 (FIG. 6A) may be about the same as, e.g., the same as, height d4.

Height d5 is typically constant (but may also vary) proceeding laterally from first and second junctions 73a, 73b of upper surface 53 of lower substrate 21 toward first and second lateral walls 79a, 79b (FIGS. 6A, 6B, and 12).

A lateral distance d6 (FIG. 12) between first and second opposed walls 63a, 63b and first and second junctions 73a, 3b is typically at least about 1 mm, at least about 1.25 mm, at least about 1.5 mm, at least about 1.75 mm, or at least about 2 mm. Lateral distance d6 may be about 10 mm or less, about 7.5 mm or less, about 5 mm or less, about 3 mm or less, or about 2.5 mm or less. A distance d7 (FIG. 12) between distal wall 79c and a distal wall 81 is typically about the same as, e.g., the same, as distance d6.

In certain embodiments, the microfluidic device can include a third depth that is less than the second depth. In some embodiment, the third depth is about half of the second depth, or less. For example, if the second depth is 75 μm, the third depth can be for example, 33 μm.

In some embodiments, the first depth corresponds or is defined by the height of the mixing well. The second depth is defined by the height of the dry reagent zone, and the third depth is defined by the height of a waste channel disposed distal to the detection zone.

In some embodiments, the microfluidic device further includes a fourth depth defined by a plateau disposed in a recess of the filter pocket. The fourth depth can be less than the first depth. The fourth depth can also be less than the second depth.

In some embodiments, the filter pocket comprises a ridge integral with the raised plateau and extending proximally from a proximal portion of a groove defined by the upper surface of the lower substrate.

In some embodiments, sloping floor portions extend laterally outward and downward to a plateau integral with the ridge.

With reference to, for example, FIGS. 10, 11 and 12, peripheral walls 79a, 79b, 79c, 79e define a periphery of a filter pocket 86 in a surface 53 of lower substrate 21. First, second, and third hydrophobic floor portions 71a, 71b, 71c and first and second sloping floor portions 69a, 69b define a floor of filter pocket 86. First, second, and third hydrophobic floor portions 71a, 71b, 71c and first and second sloping floor portions 69a, 69b are spaced apart from, e.g., below, portions of upper surface 53 of lower substrate 21 adjacent to filter pocket 86 along an axis a2 normal to upper surface 53 and/or along an axis a1 normal to lower surface 45 of upper substrate 23 (FIG. 13) when upper substrate is secured with respect to lower substrate 21. In embodiments, at least about 50%, at least about 75%, at least about 90%, at least about 95%, or essentially all of the area of first, second, and third hydrophobic floor portions 71a, 71b, 71c and first and second sloping floor portions 69a, 69b are spaced apart from, e.g., below, portions of upper surface 53 of lower substrate 21 adjacent to filter pocket 86.

Upper surface 53 of lower substrate 21 further defines a groove 87 extending from a proximal portion 93 (same as proximal floor 61), a reagent portion 95 (FIG. 11), a ramp portion 97, a detection portion 99, and a distal portion 30. First, second, and third hydrophobic floor portions 71a, 71b, 71c and first and second sloping floor portions 69a, 69b are spaced apart from, e.g., below, groove 87. In embodiments, at least about 50%, at least about 75%, at least about 90%, at least about 95%, or essentially all of the area of first, second, and third hydrophobic floor portions 71a, 71b, 71c and first and second sloping floor portions 69a, 69b are spaced apart from, e.g., below, at least a portion of groove 87, e.g., at least 50%, at least about 75%, at least about 90%, essentially all of groove 87. In embodiments, at least about 50%, at least about 75%, at least about 90%, at least about 95%, or essentially all of the area of first, second, and third hydrophobic floor portions 71a, 71b, 71c and first and second sloping floor portions 69a, 69b are spaced apart from, e.g., below, at least a portion of groove 87 disposed proximal to detection zone 43 (FIG. 10), e.g., at least 50%, at least about 75%, at least about 90%, essentially all of groove 87 disposed proximal to detection zone 43.

In some embodiments, the dry reagent zone 95 contains reagents positioned at the floor of the reagent zone, wherein the reagent zone is configured to reconstitute the dry reagents in the filtered liquid. In some embodiments, the dry reagent zone contains hydrophobic ink walls having a height that is perpendicular to capillary flow configured to maintain the sample in a hydrophilic region of the reagent zone. In some embodiments, the dry reagent zone has a width of approximately 75 μm.

Detection zone 43 of microfluidic device 20 typically includes a one or more capture zones. A capture zones is comprised of reagents, such as receptors, or devices, such as electrodes which bind or react with one or more components from the liquid sample and/or reagents combined with the liquid sample. Such binding or reaction is related to the presence or amount of target ligand in the sample. One or more detection zones 43 can be placed in the capillary channel 25 to measure the presence or amount of one or more target ligands. Reagent portion 95 of microfluidic device 20 includes one or more reagents that facilitate detection of one or more targets in a liquid sample. Exemplary reagents and techniques for depositing such reagents in reagent portion 95 are described in U.S. Pat. No. 7,824,611, which is incorporated herein by reference.

For example, as described in U.S. Pat. No. 7,824,611, texture on a device surface can facilitate drying of reagents on the surface during preparation of the device, as well as uniform placement of dried reagents on the surface as follows. A liquid reagent-containing fluid is placed in contact with the textured surface, and small reagent fluid menisci form adjacent each texture structure. Absent the presence of texture, the fluid would tend to form larger menisci at comers of the entire chamber, which when dried would produce a non-uniform layer of dried reagent. When texture structures are designed into the device, the presence of numerous small menisci leads to a more uniform layer of reagent that is dried throughout the chamber.

In embodiments, reagents, includes receptors which bind or react with one or more components from the liquid sample and/or reagents combined with the liquid sample. The reagents, such as receptors, may be immobilized on the surface of the device through covalent bonds or through adsorption. One embodiment is to immobilize receptor coated latex particles, for example of diameters ranging from about 0.1 μm to 5 μm. In addition, particles termed "nanoparticles" can also be coated with receptor and the resulting nanoparticles can be immobilized to the device through adsorption or covalent bonds. Nanoparticles are generally composed of silica, zirconia, alumina, titania, ceria, metal sols, and polystyrene and the like and the particle sizes range from about 1 nm to 100 nm. The benefit of using nanoparticles is that the surface area of the protein coating the nanoparticle as a function of the solids content is dramatically enhanced relative to larger latex particles. In one embodiment, the receptors bind to the surface through electrostatic, hydrogen bonding and/or hydrophobic interactions. Electrostatic, hydrogen bonding and hydrophobic interactions are discussed, for example, in Biochemistry 20, 3096 (1981) and Biochemistry 29, 7133 (1990). For example, the surface can be treated with a plasma to generate carboxylic acid groups on the surface. The receptor coated latex particles are preferably applied in a low salt solution, for example, 1-20 mM, and at a pH which is below the isoelectric point of the receptor. Thus, the negative character of the carboxylic acid groups and the positive charge character of the receptor latex will result in enhanced electrostatic stabilization of the latex on the surface. Hydrogen bonding and hydrophobic interactions would also presumably contribute to the stabilization and binding of the receptor latex to the surface. Magnetic fields may also be used to immobilize particles which are attracted by the magnetic field.

As discussed above, textured surfaces can serve to provide additional surface area which allows for a higher density of assay reagents to be immobilized thereon. Furthermore, a textured surface, or other surface modifications, can be provided to affect the flow characteristics of a fluid on or within the surface. For example, as disclosed herein a surface can be provided with hydrophobic regions to diminish the extent of fluid flow in the hydrophobic region, textures can be used that provide for a more uniform distribution of dried reagents on the surface, textures can be provided to modify the configuration of the meniscus at the fluid flow front, or textures can be used that provide the capillary driving force for movement of fluid within the surface.

Reagents include signal producing reagents. Such reagents include for example, a receptor specific for a target ligand adsorbed to a colloidal metal, such as a gold or selenium sol. Other reagents include ligand analogue-ligand complement conjugates to each target ligand and receptors adsorbed to latex particles with diameters of, for example, 0.1 µm to 5 µm to each target ligand, in appropriate amounts, for example, as taught by U.S. Pat. Nos. 5,028,535 and 5,089,391. The ligand complement on the conjugate can be any chemical or biochemical which does not bind to the receptors for the target ligands. Additional reagents include detergents for a washing step.

In certain embodiments, a microfluidic device further includes a waste channel 240 configured to hold excess liquid sample during a wash of the detection zone. In some embodiments, a portion of the substrate covers the waste channel and that portion covering the waste channel is printed with hydrophobic ink, the structure configured to increase flow rate and decrease wash time. In some embodiments, the waste channel has a depth of approximately 30 µm.

As used herein a target ligand refers to the binding partner to one or more receptors. Synonyms for target ligand are analyte, ligand or target analyte.

As used herein in a ligand refers to the binding partner to one or more ligand receptor(s). A synonym for ligand is analyte. For example, a ligand can comprise an antigen, a nucleotide sequence, lectin or avidin.

As used herein a ligand analogue refers to a chemical derivative of the target ligand which may be attached either covalently or noncovalently to other species, for example, to the signal development element. Ligand analogue and target ligand may be the same and both generally are capable of binding to the ligand receptor. Synonyms for ligand analogue are analyte analogue or target analyte analogue.

As used herein a ligand analogue conjugate refers to a conjugate of a ligand analogue and a signal development element. A ligand analogue conjugate can be referred to as a labeled ligand analogue.

As used herein a receptor refers to a chemical or biochemical species capable of reacting with or binding to target ligand, typically an antibody, a binding fragment, a complementary nucleotide sequence, carbohydrate, biotin or a chelate, but which may be a ligand if the assay is designed to detect a target ligand which is a receptor. Receptors may also include enzymes or chemical reagents that specifically react with the target ligand. A receptor can be referred to as a reagent or a binding member. A receptor which is neither a labeled receptor nor an immobilized receptor can be referred to as an ancillary receptor or an ancillary binding member. For example, a receptor can comprise an antibody.

As used herein a ligand receptor conjugate refers to a conjugate of a ligand receptor and a signal development element; synonyms for this term include binding member conjugate, reagent conjugate, labeled reagent or labeled binding member.

As used herein a ligand complement refers to a specialized ligand used in labeling ligand analogue conjugates, receptors, ligand analogue constructs or signal development elements.

As used herein a ligand complement receptor refers to a receptor for ligand complement and a ligand analogue-ligand complement conjugate refers to a conjugate including a ligand analogue and a ligand complement.

Ramp portion 97 of microfluidic device has a length along capillary channel 25 of 3 mm and a pitch of 14 microns per mm proceeding distally along capillary channel 25. The positive pitch decreases a height of capillary channel 25 from 75 microns prior to ramp portion 97 to 33 microns distal to ramp portion 97. In embodiments, a ramp portion may have a length of at least about 0.5 mm, at least about 1 mm, at least about 1.5 mm. A ramp portion may have a length of about 5 mm or less, about 4 mm or less, about 3.5 mm or less, about 3 mm or less, about 2 mm or less, about 1.5 mm or less. In embodiments, a pitch of the ramp portion may be at least about 10 microns per mm, at least about 12 microns per mm, at least about 14 microns per mm at least about 17.5 microns per mm. The pitch of the ramp portion may be about 30 microns per mm or less, about 25 microns per mm or less, about 20 microns per mm or less. In embodiments, the ramp portion is about 1 mm long with a pitch of 22 microns per mm proceeding distally along capillary channel 25 and decreases the height of the channel from about 55 microns proximal of the ramp portion to about 33 microns distal to the ramp portion.

In use, microfluidic device 20 is typically first removed from a sealed packaging material in which the device has been transported and/or stored. The packaging material is typically formed of a material that is resistant to an exchange of gas from an interior of the packaging material to the ambient gas surrounding the packaging material. After removal from the packaging, the microfluidic device is inserted into a reader (101, FIG. 15) configured to operate microfluidic device 20 to detect one or more targets in a liquid sample, e.g., a blood or urine sample.

In embodiments, the liquid sample is a blood sample, e.g., a blood sample obtained from a finger of a human being. The liquid sample may have a total volume of about 75 microliters or less, 50 microliters or less, 30 microliters or less, 20 microliters or less, such as about 15 microliters or less, such as about 10 microliters or less. The liquid sample may be combined with reagent, e.g., a liquid and/or a dry reagent, prior to introducing the liquid sample to the microfluidic device.

Optional Pump Feature

With reference to FIGS. 15 and 16, in certain embodiments, that system can further include a syringe pump 801 that makes a fluidic connection, e.g., a gas-tight seal, with respect to distal vent 29 of capillary channel 25 of microfluidic device 20.

Liquid sample is then applied to upper surface 35 of filter 33 via port 31. Filtered liquid (e.g., liquid that emerges from lower surface 37 of filter 33 after being applied to upper surface 35 within port 31) passes into first and second cavity portions sample cavities 75a, 75b. A high capillarity experienced by filtered liquid at first and second where lower surface 37 of filter contacts first and second opposed walls 63a, 63b draws liquid out of filter 33 and into sample cavities 75a, 75b, e.g., generally along path p2 and a path p3. First and second hydrophobic floor portions 71a, 71b, 71c prevent filtered liquid from passing beyond first and second junctions 73a, 73b and into peripheral cavity 85.

Filtered liquid moves within sample cavities 75a, 75b by capillary action to proximal opening 27 of capillary channel 25 and moves by capillary action at least a portion of the way into capillary channel 25. With the pump in fluidic connection with distal vent 29 of capillary channel 25, a volume of gas acting upon a distal gas-liquid interface 107 of the filtered liquid is confined within a volume determined by the volume of capillary channel 25 distal to interface 107 and a dead volume of the pump. As distal gas-liquid interface 107 moves distally along capillary channel 25, the volume of the confined gas decreases and the pressure of the confined gas acting upon the distal gas-liquid interface 107 increases by an amount corresponding to decreased volume. The total volume of gas confined distal to opening 27 of capillary channel 25 is about 25 microliters. By total volume of gas it is meant a volume including the volume of gas in channel 25 and the volume of gas within pump 801 in communication with capillary channel 25. In embodiments, the total volume of gas is about 50 microliters or less, about 35 microliters or less, about 30 microliters or less, or about 25 microliters or less. The total volume of gas may be at least about 10 microliters, at least about 15 microliters, at least about 20 microliters. The volume of capillary channel 25 is typically at least about 7.5 microliters, at least about 10 microliters, or at least about 12.5 microliters. The volume of capillary channel 25 may be about 25 microliters or less, about 20 microliters or less, about microliters or less, or about 15 microliters or less.

Before distal gas liquid interface 107 of the filtered liquid contacts reagent portion 41 of capillary channel 25 the gas pressure acting on distal gas liquid interface 107 increases such that the capillary force experienced by the filtered liquid is insufficient to move the filtered liquid further along the capillary channel 25 (FIG. 15).

The pressure of the gas acting upon the distal gas liquid interface of the filtered liquid is determined using a pressure sensor 103 (FIG. 11) in communication with the volume of gas enclosed distal to distal gas-liquid interface 107. Pressure sensor 103 may be configured to determine an absolute pressure of the enclosed gas, e.g., a pressure with respect to a pressure of ambient gas, e.g., a pressure of gas acting upon outer surfaces of microfluidic device 20.

In alternate embodiments, the reader actuates syringe pump 801 to increase a volume of the enclosed gas by an amount sufficient to decrease the gas pressure acting on distal gas-liquid interface 107. Capillary action draws the filtered liquid further along capillary channel 25 until distal gas liquid interface 107 contacts and then passes beyond reagent portion 41. A gas pressure acting on distal gas liquid interface 107 increases such that the capillary force experienced by the filtered liquid is insufficient to move the filtered liquid further along the capillary channel (FIG. 16).

In embodiments including a pump, after a period of time sufficient to permit the filtered liquid and reagent to react and/or combine with a reagent in reagent portion 41, the reader actuates syringe pump 801 to increase the volume of the enclosed gas by an amount sufficient to decrease the gas pressure acting on distal gas-liquid interface 107. Capillary action draws the filtered liquid further along capillary channel 25 until distal gas liquid interface 107 contacts and then passes beyond detection zone 43. A gas pressure acting on distal gas liquid interface 107 increases such that the capillary force experienced by the filtered liquid is insufficient to move the filtered liquid further along the capillary channel (FIG. 16).

Reader

A reader is structured to determine the presence and/or amount of one or more targets in a microfluidic device, as part of a microfluidic system. The reader may include a biosensor to determine the presence and/or amount of the one or more targets. The biosensor may be an electrochemical, optical, electro-optical, or acoustic mechanical detector. Referring to FIG. 15, for example, the reader may be a scanning fluorimeter, and may include a light source and light detector to determine the presence and/or amount of detectable label bound in the solid phase spots 343. In an optional embodiment as in FIG. 16, a pump 801 may be configured to control fluid flow.

In use, the total volume of filtered liquid that is drawn into capillary channel 25 is less than a total volume of the capillary channel so that filtered liquid does not exit vent 29 of microfluidic device 20.

A distal portion of capillary channel 25 includes a distal stop 111 having a capillary break 113. Liquid reaching capillary break 113 experiences a reduced capillary force reducing a tendency of the liquid from advancing further along capillary channel 25. A depth of distal stop 111 is 300 microns. The depth of distal stop 111 is typically at least about 200 microns, at least about 250 microns, or at least about 275 microns. The depth of distal stop 111 may be about 1000 microns or less, about 750 microns or less, or about 500 microns or less. A width of channel 25 within distal stop 111 is about 1 mm. Typically, the width of channel 25 within distal stop 111 is at least about 500 microns, or at least about 750 microns. The width of channel 25 within distal stop 111 may be about 2500 microns or less, about 1500 microns or less or about 1250 microns or less.

Hydrophobic Surfaces

Referring to FIG. 10, Hydrophobic surfaces of microfluidic device 20, e.g., first, second, and third hydrophobic floor portions 71a, 71b, 71c, may be made hydrophobic using hydrophobic compounds, such as aliphatic and/or aromatic compounds and various inks and polymers and the like. The compounds are generally dissolved in organic solvents or mixtures of aqueous and organic solvents. U.S. Pat. No. 7,824,611 (incorporated by reference herein) discloses suitable techniques (such as inkjet printing, spraying, silk screening, drawing, embossing and the like) that permit the application of hydrophobic zones on or within surfaces.

For example, U.S. Pat. No. 7,824,611 discloses several techniques which may be utilized to make a surface hydrophobic. For surfaces made hydrophilic, hydrophobic zones can be created by application of organic solvents that destroy the plasma treatment or denature the proteins, to recreate a native hydrophobic plastic surface or to create a hydrophobic surface by the denatured proteins, or by local heating of the surface using focused laser beams to destroy the hydrophilic nature of the surface. Alternatively, one can mask hydrophobic areas before creating a hydrophilic area by any of the foregoing methods. The areas can be masked by objects such as a template or can be masked by materials that are applied to the surface and then are subsequently removed.

In one embodiment a hydrophobic surface may be created by beginning with a hydrophobic surface, such as are found on native plastics and elastomers (polyethylene, polypropylene, polystyrene, polyacrylates, silicon elastomers and the like). In an embodiment, hydrophobic particles, may be deposited upon a surface. Such particles include latex particles, for example polystyrene latexes with diameters of between about 0.01 μm and 10 μm or hydrophobic polymers, such as polypropylene, polyethylene, polyesters and the like. In another embodiment, a hydrophobic surface may be created by application of a hydrophobic chemical, such as an ink or along chain fatty acid, or a hydrophobic decal to the desired zone. The hydrophobic chemical or decal is generally not soluble or is poorly soluble in the reaction mixture. In yet another preferred embodiment, the hydrophobic surface may be formed by changing a hydrophilic surface to a hydrophobic surface. For example, hydrophobic surfaces made hydrophilic by plasma treatment can be converted back to a hydrophobic surface by the application of solvents, ultraviolet light or heat and the like. These treatments can act to change the molecular structure of the hydrophilic, plasma modified surface back to a hydrophobic form.

As discussed above, hydrophobic compounds, such as aliphatic and/or aromatic compounds and various inks and polymers and the like can be used for the creation of hydrophobic zones in accordance with the invention. The compounds are generally dissolved in organic solvents or mixtures of aqueous and organic solvents. One skilled in the art will recognize that a variety of techniques known in the art (such as inkjet printing, spraying, silk screening, drawing, embossing and the like) are techniques that permit the application of hydrophobic zones on or within surfaces.

Components of microfluidic device 20 (e.g., lower and upper substrates 21, 23) can be prepared from copolymers, blends, laminates, metallized foils, metallized films or metals. Alternatively, microfluidic device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Lower and upper substrates 21, 23 may be secured with respect to one another the various recesses and grooves sealed and the capillary cavities and channels formed by a number of techniques, including but not limited to, gluing, welding by ultrasound, riveting and the like.

A number of embodiments of the invention have been described. Nevertheless, it will be understood that various modifications may be made without departing from the spirit and the scope of the invention.

What is claimed is:

1. A microfluidic device comprising:
   a port configured to receive a liquid sample, a filter pocket, a mixing well, and a capillary flow channel;
   wherein the capillary flow channel comprises a proximal opening, a distal opening, a dry reagent zone, a pinch region, and a detection zone;
   wherein the filter pocket comprises a filter and disposed substantially at the proximal opening;
   wherein the mixing well comprises a length, a width, a height, and a perimeter, the width decreasing from a central portion of the mixing well toward the perimeter along at least two opposed directions, wherein the mixing well is disposed distal to the filter pocket;
   wherein the dry reagent zone containing a reagent, the dry reagent zone disposed distal to the mixing well;
   wherein the pinch region is configured to redirect flow, wherein the pinch region is disposed distal to the dry reagent zone and has a width that is less than that of the capillary flow channel;
   wherein the pinch region has a width that is at most half the width of the capillary flow channel;
   wherein the detection zone is disposed distal to a fluid resistance feature,
   wherein the distal opening is tapered to control a flow rate, and wherein the filter pocket, the mixing well, the dry reagent zone, pinch region, and the detection zone are in fluidic communication.

2. The microfluidic device of claim 1, wherein the filter pocket comprises a sample inlet having a recess configured to receive a liquid sample, a filter landing, and a vent configured to permit air to be displaced upon receiving the liquid sample.

3. The microfluidic device of claim 2, wherein the filter landing includes a raised plateau extending from a distal edge of the filter pocket.

4. The microfluidic device of claim 2, wherein the filter pocket further comprises a catwalk strip disposed for directing a fluid deposited at the sample inlet to the filter landing.

5. The microfluidic device of claim 1, wherein the mixing well is dimensioned to move a filtered liquid sample by capillary action.

6. The microfluidic device of claim 1, wherein the dry reagent zone contains walls with a hydrophobic ink.

7. The microfluidic device of claim 1, wherein the pinch region is configured with a lobe, optionally wherein the pinch region comprises a portion of the capillary flow channel that is lobed in a direction that is substantially perpendicular to a length of the microfluidic device.

8. The microfluidic device of claim 1, wherein the detection zone contains at least one solid phase capture spot configured to bind a specific analyte.

9. The microfluidic device of claim 1, further comprising two or more solid phase capture spots arranged in a series along a length of the detection zone.

10. The microfluidic device of claim 8, wherein the at least one solid phase capture spot provides a signal measured by a reader.

11. The microfluidic device of claim 1, further comprising a waste channel distal to the detection zone.

12. The microfluidic device of claim 11, wherein a portion of a substrate covers the waste channel and that portion is printed with hydrophobic ink that increases flow rate and decreases wash time.

13. The microfluidic device of claim 1, wherein the capillary flow channel is disposed between an upper substrate and a lower substrate.

14. The microfluidic device of claim 13, wherein the lower substrate comprises a first portion having a first depth and a second portion having a second depth that is less than the first depth.

15. The microfluidic device of claim 14, wherein a portion having a first depth is convex and a portion having a second depth is planar.

16. The microfluidic device of claim 1, wherein the filter pocket is configured to move liquid by capillary action along the capillary flow channel and into the mixing well of the capillary flow channel.

17. The microfluidic device of claim 7, wherein the mixing well is configured to move liquid by capillary action along the capillary flow channel and into the pinch region of the capillary flow channel.

18. The microfluidic device of claim 1, wherein the mixing well comprises a depth that is greater than a depth of the capillary flow channel.

19. A method for determining a presence or an absence of a cardiac troponin in a patient sample, comprising:

placing a blood sample on a microfluidic device of claim 1 to label the cardiac troponin, if present in the patient sample, with a label comprising a binding partner for the cardiac troponin and a detectable moiety; and detecting a presence of cardiac troponin in the patient sample by determining a presence or an absence of the label, wherein detection of the presence of the label indicates the presence of cardiac troponin in the patient sample, wherein an assay has a limit of quantitation of about 3 $\mu$g/mL with a coefficient of variation of less than about 20%.

20. The method of claim 19, wherein the cardiac troponin is cardiac troponin I (cTnI).

21. The method of claim 19, wherein the cardiac troponin is cardiac troponin T (cTnT).

22. The method of claim 19, wherein the cardiac troponin is a complex of cTnI and cTnT.

23. The microfluidic device of claim 1, wherein the mixing well is substantially bowl-shaped.

*   *   *   *   *